(12) United States Patent
Berkenstam et al.

(10) Patent No.: US 10,130,713 B2
(45) Date of Patent: Nov. 20, 2018

(54) COCRYSTALLINE DHEA FORMULATIONS

(71) Applicant: University of Houston System, Houston, TX (US)

(72) Inventors: Anders Berkenstam, Houston, TX (US); Edward Kuczynski, Houston, TX (US); Alf S. Andersson, Houston, TX (US); Jan-Ake Gustafsson, Houston, TX (US); Carly Sue Filgueira, Houston, TX (US)

(73) Assignees: THE METHODIST HOSPITAL, Houston, TX (US); UNIVERSITY OF HOUSTON SYSTEM, Houston, TX (US)

( * ) Notice: Subject to any disclaimer, the term of this patent is extended or adjusted under 35 U.S.C. 154(b) by 0 days.

(21) Appl. No.: 14/257,594

(22) Filed: Apr. 21, 2014

(65) Prior Publication Data

US 2014/0315833 A1  Oct. 23, 2014

Related U.S. Application Data

(60) Provisional application No. 61/813,920, filed on Apr. 19, 2013.

(51) Int. Cl.

| A61K 47/48 | (2006.01) |
| C07C 49/727 | (2006.01) |
| A61K 9/00 | (2006.01) |
| C07C 55/12 | (2006.01) |
| C07C 57/145 | (2006.01) |
| C07C 59/255 | (2006.01) |
| C07J 1/00 | (2006.01) |
| A61K 47/54 | (2017.01) |
| A61K 47/69 | (2017.01) |

(52) U.S. Cl.
CPC ...... *A61K 47/48092* (2013.01); *A61K 9/0053* (2013.01); *A61K 47/542* (2017.08); *A61K 47/549* (2017.08); *A61K 47/6921* (2017.08); *C07C 55/12* (2013.01); *C07C 57/145* (2013.01); *C07C 59/255* (2013.01); *C07J 1/0011* (2013.01); *C07B 2200/13* (2013.01)

(58) Field of Classification Search
CPC ........ A61K 47/48092; A61K 47/48038; C07C 49/727
USPC ................ 514/23, 178; 536/1.11; 552/650
See application file for complete search history.

(56) References Cited

U.S. PATENT DOCUMENTS

| 7,045,513 B1 | 5/2006 | Parasrampuria | |
| 2006/0004076 A1 | 1/2006 | Patel | |
| 2006/0009433 A1* | 1/2006 | Yao et al. | 514/178 |
| 2007/0032462 A1 | 2/2007 | Criton | |
| 2009/0069279 A1 | 3/2009 | Astruc | |
| 2010/0204204 A1* | 8/2010 | Zaworotko et al. | 514/212.03 |

FOREIGN PATENT DOCUMENTS

EP  1140110  6/2003

OTHER PUBLICATIONS

Bhatt et al. Co-crystal formation and the determination of absolute configuration. CrystEngComm 10:1747-1749, 2008.*
International Search Report and Written Opinion for PCT/US2014/034807 dated Aug. 14, 2014 ( 15 pages).

* cited by examiner

*Primary Examiner* — Yih-Horng Shiao
(74) *Attorney, Agent, or Firm* — Conley Rose, P.C.

(57) ABSTRACT

A cocrystalline DHEA composition with at least one additional coformer is disclosed for therapeutic formulations. The cocrystalline DHEA/coformer formulation including at least one coformer chosen from the group consisting of glutaric acid, maleic acid, tartaric acid, fructose, and wherein the L-isomer of tartaric acid and the D-isomer of fructose are utilized. The cocrystalline DHEA/coformer formulations include certain excipients as a solubilizer or inhibitor.

15 Claims, 59 Drawing Sheets

| Form | Nature | References |
|---|---|---|
| FI | anhydrate | • Kuhnert-Brandstätter, *Thermomicroscopy in the Analysis of Pharmaceuticals*; Pergamon Press: Oxford, 1971.<br>• Chang *et al. J. Pharm. Sci.* 1995, *84*, 1169-1179.<br>• Caira *et al. J. Chem. Crystallogr.* 1995, *25*, 393-400. |
| FII | anhydrate | • Kuhnert-Brandstätter, *Thermomicroscopy in the Analysis of Pharmaceuticals*; Pergamon Press: Oxford, 1971.<br>• Chang *et al. J. Pharm. Sci.* 1995, *84*, 1169-1179.<br>• Bhacca *et al. J. Chem. Crystallogr.* 1996, *26*, 483-487. |
| FIII | anhydrate | • Kuhnert-Brandstätter, *Thermomicroscopy in the Analysis of Pharmaceuticals*; Pergamon Press: Oxford, 1971.<br>• Chang *et al. J. Pharm. Sci.* 1995, *84*, 1169-1179. |
| FIV | anhydrate | • Kuhnert-Brandstätter, *Thermomicroscopy in the Analysis of Pharmaceuticals*; Pergamon Press: Oxford, 1971. |
| FV | anhydrate | • Chang *et al. J. Pharm. Sci.* 1995, *84*, 1169-1179. |
| FVI | anhydrate | • Stahly *et al. Cryst. Growth. Des.* 2006, *6*, 925-932. |
| S1 | ¼ hydrate | • Chang *et al. J. Pharm. Sci.* 1995, *84*, 1169-1179.<br>• Caira *et al. J. Chem. Crystallogr.* 1995, *25*, 393-400. |
| S2 | monohydrate | • Chang *et al. J. Pharm. Sci.* 1995, *84*, 1169-1179.<br>• Cox *et al. Acta Cryst.* 1990, *C46*, 334-336. |
| S3 | monohydrate | • Chang *et al. J. Pharm. Sci.* 1995, *84*, 1169-1179. |
| S4 | hemi-methanolate | • Chang *et al. J. Pharm. Sci.* 1995, *84*, 1169-1179.<br>• Caira *et al. J. Chem. Crystallogr.* 1995, *25*, 393-400. |

FIGURE 2

| Coformer | Sample No | Method | Amount (mg) | XRPD Filename | XRPD Result |
|---|---|---|---|---|---|
| D-fructose | 89-21-3 | Grind, melt, cool to crystallize | 42.2 | RXRPD3132 | Cocrystal form 1 |
| D-fructose | 89-24-1 | Grind, melt, cool to crystallize | 94.8 | RXRPD3167 | Cocrystal form 2 |
| D-fructose | 86-73-1 | melt/quench | 87 | RXRPD3528 | Cocrystal form 3 |
| D-fructose | 96-73-3 | melt/quench | 357 | RXRPD3832 | Cocrystal form 4 |
| D-fructose | 96-73-4 | melt/quench | 218 | RXRPD3834 | Cocrystal form 5 |
| maleic acid | 89-7-4 | rotovap acetone solution | 125 | RXRPD3045 | Cocrystal form 6 |
| maleic acid | 86-72-3 | rotovap acetone solution | 160 | RXRPD3518 | Cocrystal form 7 |
| maleic acid | 96-73-2 | rotovap acetone solution | 384 | RXRPD3829 | Cocrystal form 8 |
| glutaric acid | 89-7-3 | rotovap acetone solution | 140 | RXRPD3044 | Cocrystal form 9 |
| glutaric acid | 86-72-2 | rotovap acetone solution | 152 | RXRPD3517 | Cocrystal form 10 |
| glutaric acid | 96-73-1 | rotovap acetone solution | 404 | RXRPD3828 | Cocrystal form 11 |
| L-tartaric acid | 89-7-1 | Slurry in THF:heptane (1:2) | 155 | RXRPD3072 | Cocrystal form 12 |
| L-tartaric acid | 96-76-1 | Slurry in THF:heptane (1:2) | 176 | RXRPD3860 | Cocrystal form 13 |

FIGURE 4

| Coformer | Cocrystal Sample No. | Duration of Slurry | XRPD File Name | XRPD Page No. | XRPD Result |
|---|---|---|---|---|---|
| D-fructose | 86-73-1 | overnight | RXRPD3563 | 29 | unknown pattern |
| glutaric acid | 86-72-2 | overnight | RXRPD3561 | 29 | DHEA form FII[a] + cocrystal + unknown |
| maleic acid | 86-72-3 | overnight | RXRPD3562 | 29 | DHEA form FII[a] + cocrystal + unknown |
| L-tartaric acid | 86-78-1 | 1 minute | RXRPD3611 | 30 | DHEA form S2[b] | a. Anhydrate. b. Monohydrate.

FIGURE 9

| Time | Sample No. | HPLC File Name | HPLC Page No. | Solubility (µg/mL) | Average Solubility (µg/mL) |
|---|---|---|---|---|---|
| 1 min | 96-74-2 | HPLC1252 | 33 | 30 | 30 |
|  |  | HPLC1253 | 34 | 30 |  |
| 2.5 min | 96-74-3 | HPLC1254 | 35 | 27 | 27 |
|  |  | HPLC1255 | 36 | 27 |  |
| 4 min | 96-74-4 | HPLC1256 | 37 | 28 | 28 |
|  |  | HPLC1257 | 38 | 28 |  |
| 5.5 min | 96-74-5 | HPLC1258 | 39 | 23 | 23 |
|  |  | HPLC1259 | 40 | 23 |  |
| 7 min | 96-74-6 | HPLC1260 | 41 | 29 | 29 |
|  |  | HPLC1261 | 42 | 28 |  |
| 10 min | 96-50-2 | HPLC1199 | 43 | 33 | 33 |
|  |  | HPLC1200 | 44 | 33 |  |
| 30 min | 96-50-3 | HPLC1201 | 45 | 22 | 22 |
|  |  | HPLC1202 | 46 | 22 |  |
| 1 hr | 96-50-4 | HPLC1203 | 47 | 23 | 23 |
|  |  | HPLC1204 | 48 | 23 |  |
| 2 hr | 96-50-5 | HPLC1205 | 49 | 19 | 19 |
|  |  | HPLC1206 | 50 | 18 |  |
| 5 hr | 96-50-6 | HPLC1207 | 51 | 18 | 18 |
|  |  | HPLC1208 | 52 | 17 |  |
| 22 hr[b] | 96-50-1 | HPLC1214 | 53 | 17 | 17 |
|  |  | HPLC1215 | 54 | 17 |  | a. Sample TL876. Dissolution medium was water buffered to pH 6.8.
b. At 22 hours the pH of solution was measured to be 6.8 and XRPD analysis of the solid (RXRPD3777, page 30) showed it was DHEA monohydrate S1.

FIGURE 10

| Time[a] | Sample No. | HPLC File Name | HPLC Page No. | Solubility (µg/mL) | Average Solubility (µg/mL) |
|---|---|---|---|---|---|
| 1 min | 96-74-14 | HPLC1272 | 55 | 55 | 55 |
| | | HPLC1273 | 56 | 55 | |
| 2.5 min | 96-74-15 | HPLC1274 | 57 | 57 | 58 |
| | | HPLC1275 | 58 | 59 | |
| 4 min | 96-74-16 | HPLC1276 | 59 | 50 | 50 |
| | | HPLC1277 | 60 | 49 | |
| 5.5 min | 96-74-17 | HPLC1278 | 61 | 64 | 64 |
| | | HPLC1279 | 62 | 63 | |
| 7 min | 96-74-18 | HPLC1280 | 63 | 56 | 56 |
| | | HPLC1281 | 64 | 55 | |
| 10 min | 96-54-2 | HPLC1218 | 65 | 25 | 25 |
| | | HPLC1219 | 66 | 25 | |
| 30 min | 96-54-3 | HPLC1220 | 67 | 19 | 20 |
| | | HPLC1221 | 68 | 20 | |
| 1 hr | 96-54-4 | HPLC1222 | 69 | 17 | 17 |
| | | HPLC1223 | 70 | 17 | |
| 2 hr | 96-54-5 | HPLC1224 | 71 | 17 | 17 |
| | | HPLC1225 | 72 | 16 | |
| 5 hr | 96-54-6 | HPLC1226 | 73 | 17 | 18 |
| | | HPLC1227 | 74 | 18 | |
| 22 hr[c] | 96-54-1 | HPLC1243 | 75 | 17 | 17 |
| | | HPLC1244 | 76 | 17 | | a. Dissolution medium was water buffered to pH 6.8.
b. Starting material for experiment with time points 1-7 min was 96-73-4; starting material for experiment with time points 10 min through 22 hours was 86-73-1.
c. At 22 hours the pH of solution was measured to be 6.6 and XRPD analysis of the solid (RXRPD3795, page 31) showed it was DHEA monohydrate S1.

FIGURE 11

| Time[b] | Sample No. | HPLC File Name | HPLC Page No. | Solubility (μg/mL) | Average Solubility (μg/mL) |
|---|---|---|---|---|---|
| 1 min | 96-74-8 | HPLC1262 | 77 | 35 | 35 |
| | | HPLC1263 | 78 | 34 | |
| 2.5 min | 96-74-9 | HPLC1264 | 79 | 25 | 25 |
| | | HPLC1265 | 80 | 24 | |
| 4 min | 96-74-10 | HPLC1266 | 81 | 19 | 19 |
| | | HPLC1267 | 82 | 19 | |
| 5.5 min | 96-74-11 | HPLC1268 | 83 | 21 | 21 |
| | | HPLC1269 | 84 | 20 | |
| 7 min | 96-74-12 | HPLC1270 | 85 | 22 | 22 |
| | | HPLC1271 | 86 | 21 | |
| 10 min | 96-51-2 | HPLC1189 | 87 | 18 | 19 |
| | | HPLC1190 | 88 | 19 | |
| 30 min | 96-51-3 | HPLC1191 | 89 | 19 | 19 |
| | | HPLC1192 | 90 | 19 | |
| 1 hr | 96-51-4 | HPLC1193 | 91 | 18 | 18 |
| | | HPLC1194 | 92 | 18 | |
| 2 hr | 96-51-5 | HPLC1195 | 93 | 17 | 17 |
| | | HPLC1196 | 94 | 17 | |
| 5 hr | 96-51-6 | HPLC1197 | 95 | 17 | 17 |
| | | HPLC1198 | 96 | 17 | |
| 22 hr[c] | 96-51-1 | HPLC1216 | 97 | 18 | 18 |
| | | HPLC1217 | 98 | 17 | | a. Dissolution medium was water buffered to pH 6.8.
b. Starting material for experiment with time points 1–7 min was 96-73-1; starting material for experiment with time points 10 min through 22 hours was 86-72-2.
c. At 22 hours the pH of solution was measured to be 5.0 and XRPD analysis of the solid (RXRPD3778, page 31) showed it was DHEA monohydrate S1.

FIGURE 12

| Time[b] | Sample No. | HPLC File Name | HPLC Page No. | Solubility (µg/mL) | Average Solubility (µg/mL) |
|---|---|---|---|---|---|
| 1 min | 96-84-2 | HPLC1322 | 99 | 67 | 67 |
| | | HPLC1323 | 100 | 66 | |
| 2.5 min | 96-84-3 | HPLC1324 | 101 | 37 | 37 |
| | | HPLC1325 | 102 | 37 | |
| 4 min | 96-84-4 | HPLC1326 | 103 | 29 | 30 |
| | | HPLC1327 | 104 | 30 | |
| 5.5 min | 96-84-5 | HPLC1328 | 105 | 27 | 27 |
| | | HPLC1329 | 106 | 27 | |
| 7 min | 96-84-6 | HPLC1330 | 107 | 27 | 27 |
| | | HPLC1331 | 108 | 27 | |
| 10 min[b] | 96-84-1 | not determined | | | | a. Starting material was 96-73-2. Dissolution medium was water buffered to pH 6.8.
b. At 10 minutes XRPD analysis of the solid (RXRPD3898, page 32) showed it was DHEA monohydrate S1.

FIGURE 13

| Time[b] | Sample No. | HPLC File Name | HPLC Page No. | Solubility (µg/mL) | Average Solubility (µg/mL) |
|---|---|---|---|---|---|
| 1 min | 96-79-2 | HPLC1288 | 109 | 27 | 28 |
| | | HPLC1289 | 110 | 29 | |
| 2.5 min | 96-79-3 | HPLC1290 | 111 | 22 | 23 |
| | | HPLC1291 | 112 | 23 | |
| 4 min | 96-79-4 | HPLC1292 | 113 | 23 | 24 |
| | | HPLC1293 | 114 | 24 | |
| 5.5 min | 96-79-5 | HPLC1294 | 115 | 23 | 24 |
| | | HPLC1295 | 116 | 24 | |
| 7 min | 96-79-6 | HPLC1296 | 117 | 23 | 24 |
| | | HPLC1297 | 118 | 24 | |
| 10 min[b] | 96-79-1 | not determined | | | | a. Starting material was 96-76-1. Dissolution medium was water buffered to pH 6.8.
b. At 10 minutes XRPD analysis of the solid (RXRPD3861, page 32) showed it exhibited a pattern that does not match those of the cocrystal or any known form of DHEA. The nature of that solid is currently unknown.

FIGURE 14

| Excipient | Composition | Function | Provider |
|---|---|---|---|
| PEG-6000 | polyethylene glycol | inhibitor | Hampton Research |
| Plasdone S-630 | copolymer of vinylpyrrolidone and vinyl acetate | inhibitor | ISP Technologies |
| Polysorbate 80 | polyoxyethylene sorbitan mono-oleate ester | solubilizer | Fisher Scientific |
| PVP | polyvinylpyrrolidone | inhibitor | Fisher Scientific |

| Time (min) | Sample No. | HPLC File Name | HPLC Page No. | Solubility (µg/mL) | Average Solubility |
|---|---|---|---|---|---|
| 2 | 141-87-2A | 1699 | 8 | 22 | 24 |
|  |  | 1700 | 9 | 25 |  |
| 5 | 141-87-2B | 1701 | 10 | 33 | 34 |
|  |  | 1702 | 11 | 35 |  |
| 10 | 141-87-2C | 1703 | 12 | 42 | 42 |
|  |  | 1704 | 13 | 42 |  |
| 15 | 141-87-2D | 1705 | 14 | 51 | 51 |
|  |  | 1706 | 15 | 51 |  |
| 25 | 141-87-2E | 1707 | 16 | 55 | 55 |
|  |  | 1708 | 17 | 54 |  |
| 40 | 141-87-2F | 1709 | 18 | 60 | 60 |
|  |  | 1710 | 19 | 59 |  |
| 70 | 141-87-2G | 1711 | 20 | 69 | 68 |
|  |  | 1712 | 21 | 67 |  |
| 130 | 141-87-2H | 1713 | 22 | 60 | 61 |
|  |  | 1714 | 23 | 62 |  |
| 180 | 141-87-2I | 1715 | 24 | 60 | 60 |
|  |  | 1716 | 25 | 60 |  |
| 240 | 141-87-2J | 1717 | 26 | 60 | 60 |
|  |  | 1718 | 27 | 59 |  |
| 330 | 141-87-2K | 1719 | 29 | 56 | 56 |
|  |  | 1720 | 30 | 56 |  |

FIGURE 46

COCRYSTALLINE DHEA FORMULATIONS

CROSS-REFERENCE TO RELATED APPLICATIONS

This application claims priority to U.S. Provisional Patent Application No. 61/813,920 filed on Apr. 19, 2013 and titled "Cocrystalline DHEA Formulations," the entire disclosure of which is incorporated herein by reference.

STATEMENT REGARDING FEDERALLY SPONSORED RESEARCH OR DEVELOPMENT

Not applicable.

BACKGROUND

Dehydroepiandrosterone (DHEA) is an endogenous steroid hormone in higher primates, such as man, and is secreted by the adrenal glands, and possibly the testes. It is the most abundant steroid in humans, but no single specific receptor for DHEA has been identified. One of the main functions of DHEA is to act as a metabolic intermediate in the biosynthesis of androgens and estrogens. The serum levels of DHEA and its sulfated form, DHEA-S, peak in the early twenties and the levels then steadily decline beginning in the early thirties at a rate of about 5% per year. The decline in serum DHEA levels in both women and men is highly variable and the mechanism remains unknown.

DHEA and DHEA-S have been implicated in a number of biological processes such as a stimulatory effect on bone mineral density, a favorable effect on treating vaginal atrophy when applied locally, and control of muscle mass and strength, insulin sensitivity, and serum lipid levels. In the central nervous system (CNS), DHEA is recognized as a neurosteroid reaching the brain from systemic circulation. DHEA exerts its effects on the brain through multiple direct and indirect mechanisms. DHEA is believed to act directly with N-methyl-D-aspartate (NMDA) receptors, γ-aminobutyric acid (GABA) type A receptors and sigma receptors to regulate neuronal excitability. Further, DHEA can be metabolized in the CNS to both androgens and estrogens and modulate neuronal activity.

Although banned from use in athletic competitions as a pro-drug and a physician's prescription is required to obtain DHEA in some countries, the U.S. Food and Drug Administration currently considers DHEA to be a dietary supplement. As a dietary supplement, there is no regulation on the quantity, quality, or the purity of the DHEA in commercial formulations. Further, DHEA efficacy in treating medical conditions or diseases has not been completely elucidated, in part, because it exhibits poor solubility in aqueous solutions, rapid metabolism, and minimal oral bioavailability.

SUMMARY

Disclosed is a combination of DHEA and at least one coformer, in a cocrystalline therapeutic formulation. The cocrystalline DHEA/coformer composition including at least one of the group consisting of glutaric acid, maleic acid, tartaric acid, fructose, and wherein the L-isomer of tartaric acid and the D-isomer of fructose are utilized. In some formulations, there are additional pharmaceutically acceptable excipients in order to increase oral bioavailability.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIG. 2 illustrates a table of the known DHEA crystalline forms.

FIG. 4 illustrates a table of the coformers and the method of cocrystallization according to an exemplary embodiment of the present disclosure.

FIG. 9 illustrates a table of the time necessary for conversion of the cocrystals to DHEA as a result of creating an aqueous slurry of the cocrystalline formulations in water according to an exemplary embodiment of the present disclosure.

FIG. 10 illustrates a dissolution table for a DHEA polymorph form I (FI) according to an exemplary embodiment of the present disclosure.

FIG. 11 illustrates a dissolution table for a DHEA/D-fructose cocrystalline formulation according to an exemplary embodiment of the present disclosure.

FIG. 12 illustrates a dissolution table for a DHEA/glutaric acid cocrystalline formulation according to an exemplary embodiment of the present disclosure.

FIG. 13 illustrates a dissolution table for a DHEA/maleic acid cocrystalline formulation according to an exemplary embodiment of the present disclosure.

FIG. 14 illustrates a dissolution table for a DHEA/L-tartaric acid cocrystalline formulation according to an exemplary embodiment of the present disclosure.

FIG. 46 illustrates a table correlating the sample data, solubility and page number from HPLC 1699 through HPLC 1720.

DETAILED DESCRIPTION

OVERVIEW. Dehydroepiandrosterone (DHEA) is an endogenous steroid hormone produced by the adrenal cortex. Active steroids are synthesized in peripheral intracrine organs such as the CNS from the inactive precursors DHEA and its sulfated form, DHEA-S. Through its metabolism in glia cells, astrocytes, and other tissues to estrogens and androgens, DHEA also affects the corresponding receptors. For example, DHEA is metabolized into the estrogen 5-androstene-3β,17β-diol (hereinafter, ADIOL). ADIOL is an estrogen receptor β (hereinafter, ERβ) agonist that recently has been shown to inhibit neuroinflammation, particularly in the central nervous system (CNS). However, DHEA's exhibited insolubility in aqueous matrices, such as found in vivo, inhibits the formulation of a viable therapeutic agent against diseases in which ERβ has been implicated in the pathophysiology. Representative diseases include, but are not limited to, neurodegenerative diseases including amyotrophic lateral sclerosis (ALS), Parkinson's disease (PD), and multiple sclerosis (MS).

Further, DHEA administration has been shown to inhibit tumor development and proliferation while inducing apoptosis in certain malignant tumors for both humans and certain animal models, due in part to the same metabolite, ADIOL, that has CNS anti-inflammatory effects. Due to the inverse relationship between DHEA and DHEA-S serum levels and the incidence of cardiovascular disease, DHEA has also been implicated in various cardiovascular diseases. In addition, DHEA may be used to treat pulmonary hypertension (PH), as DHEA administration has been associated with increased survival rates in PH animal models. Likewise, DHEA administration inhibits certain parasitic infections due to the inhibition of glucose-6-phosphate dehydrogenase (G6PDH) that is essential for parasite protection against oxidative stress and overall survival.

Figure 1:
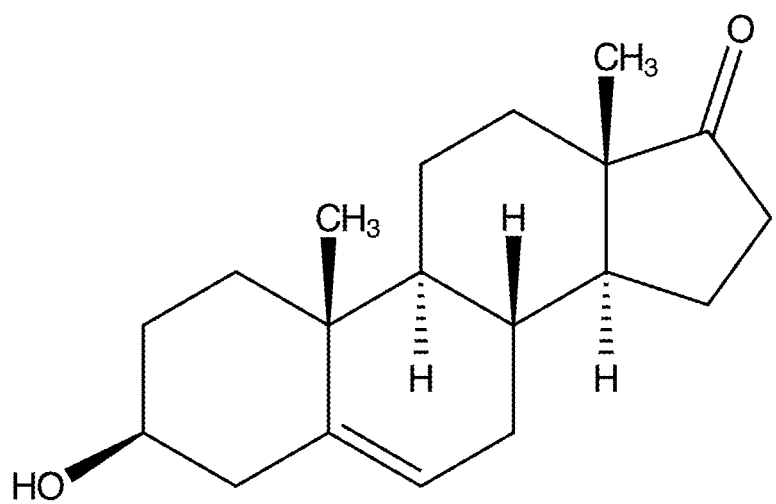
FIG. 1 illustrates the chemical structure of dehydroepiandrosterone (DHEA).

The present disclosure relates to formulations comprising DHEA as an active pharmaceutical ingredient (API). FIG. 1 illustrates the chemical structure of DHEA according to the present disclosure. DHEA is presently known to exist in at least ten crystalline forms, which are illustrated in FIG. 2. In the presently disclosed compositions, the DHEA comprises the polymorph form I (FI) and polymorph form II (FII), the anhydrous crystalline forms of DHEA. Without limitation by any particular theory, FI and FII demonstrate the most highly ordered crystals of solid DHEA.

Further, the formulations of the present disclosure comprise at least one additional compound referred to hereinafter as a "crystalline coformer(s)." Generally, the crystalline coformer is also a solid, such as a powder, a crystal, or a crystalline powder. Generally, the coformers are any molecules that form cocrystalline formulations with DHEA. As examples disclosed herein, the cocrystalline formulations comprise DHEA and a coformer chosen from the group consisting of glutaric acid, maleic acid, tartaric acid, and fructose. More specifically, the L-isomer of tartaric acid and the D-isomer of fructose are utilized in compositions comprising tartaric acid and fructose, respectively.

Without limitation by any particular theory, the cocrystalline formulations improve the chemical and physical properties of DHEA when the two compounds are crystallized concurrently. DHEA cocrystalline formulations are chosen in order to improve such properties as dissolution rates in aqueous fluids, solubility, storage stability, and ease of production of the DHEA formulations. In certain instances, the cocrystalline formulations are chosen to enhance dissolution of DHEA. In instances, enhanced dissolution of DHEA comprises increased concentration in solution for extended periods of time.

Further, the formulations of the present disclosure comprise at least one pharmaceutically approved excipient. Generally, the excipient or carrier comprises any inert or non-reactive compound that may be used in conjunction with a cocrystalline formulation comprising DHEA to enhance its physicochemical and pharmacological properties. As examples disclosed herein, the excipients may be chosen from the group consisting of polyethylene glycol (PEG), poly-vinylpyrrolidone (PVP), vinylpyrrolidone-vinylacetate copolymer (e.g. PLASDONE S-630), and polyoxyethylene-sorbitan-mono-oleate ester (e.g. POLYSORBATE 80).

Without limitation by any particular theory, the cocrystalline formulations including an excipient improve the chemical and physical properties of DHEA when the two compounds are crystallized concurrently and mixed with an excipient. DHEA cocrystalline/excipient formulations are chosen in order to improve the properties thereof including dissolution rates in aqueous fluids, solubility, storage stability, and ease of production of the DHEA formulations. In certain instances, the cocrystalline formulations are chosen to enhance dissolution of DHEA. In instances, enhanced dissolution of DHEA comprises increased concentration in solution for extended periods of time.

In more detail, in crystalline systems where the active pharmaceutical ingredient (API), such as DHEA, is placed in solution, rapidly dissolves, and subsequently recrystallizes with increased concentrations in solution, the recrystallization is a result of the concentration of the API becoming supersaturated. As used herein, supersaturation is the concentration of the API exceeding the saturation point in solution and beginning recrystallization. The result is a decreased time of the API in solution, and in the case of a chemotherapeutic composition, decreased bioavailability. As used herein, the bioavailability of a chemotherapeutic is the duration that the API is available for absorption from an aqueous solution, such as in vivo aqueous solution or the blood stream. More specifically, coformers and excipients incorporated into the cocrystalline formulations disclosed herein delay the recrystallization of the API such as DHEA, maintain the supersaturation of the aqueous solution, provide increased time for absorption and thus, increase bioavailability in vivo.

Figure 3:
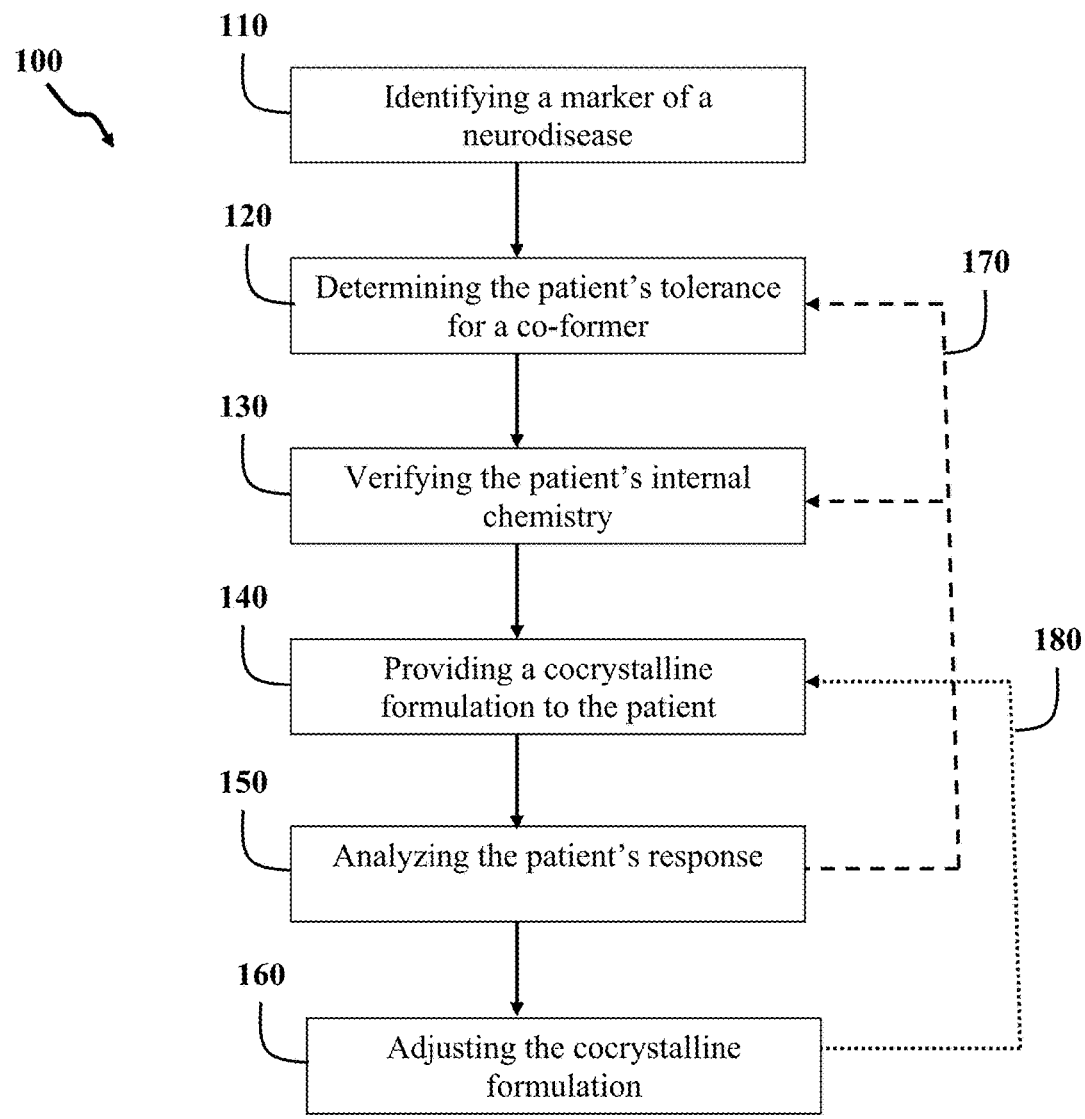
FIG. 3 illustrates a method for administering a DHEA composition to a patient.

ADMINISTRATION. Referring now to FIG. 3, there is shown an exemplary method 100 of administering a therapeutic agent comprising a cocrystalline formulation according to the present disclosure. Generally, the method 100 comprises identifying 110 at least one marker of a neurodisease in a patient, determining 120 the patient's tolerance for at least one cocrystalline formulation, verifying 130 the patient's internal chemistry, providing 140 a concentration of a cocrystalline formulation to the patient, analyzing 150 the patient's response, and adjusting 160 the concentration of the cocrystalline formulation.

More specifically, identifying 110 at least one marker of a neurological disease in a patient comprises identifying at least one symptom of a neurological disease or neuropathology that is at least partially treatable or mitigated by DHEA. The at least one symptom may comprise any physical, chemical, biochemical, or behavioral symptom, or a genetic marker indicative of the neurological disease. Exemplary neurological diseases or neuropathologies comprise a neurodegenerative or a neuroinflammatory condition, such as but not limited to amyotrophic lateral sclerosis (ALS), Parkinson's disease (PD), and multiple sclerosis (MS).

More specifically, determining 120 the patient's tolerance for at least one cocrystalline formulation comprises determining if the patient has allergies, immune response, irritation, or other negative responses to the formulation. Also, verifying 130 the patient's internal chemistry comprises determining the aqueous conditions of the patient's body in which the cocrystalline formulation will dissolve in order to suitably deliver the DHEA into the bloodstream of the patient. Additionally, verifying 130 the patient's internal chemistry comprises determining the concentration of free DHEA circulating in the bloodstream. Alternatively, the method 100 may comprise excluding the steps of determining 120 the patient's tolerance and verifying 130 the patient's internal chemistry. Further, the method 100 may comprise verifying 130 the patient's internal chemistry prior to determining 120 the patient's tolerance.

Providing 140 a concentration of a cocrystalline formulation to the patient comprises administering a therapeutically effective amount of the cocrystalline DHEA formulation. The therapeutically effective amount of the cocrystalline DHEA is predetermined from the previous steps of the method 100. Without limitation by any theory, the cocrystalline DHEA formulation may be administered as a subcutaneous, an intravenous, an intramuscular, an oral, or an inhaled dosage.

Analyzing 150 the patient's response comprises subjective and objective feedback from the patient. Subjective feedback includes the sensation of improvement in the symptoms experienced by the patient. Objective feedback includes free concentrations of the DHEA in the patient's tissues or bodily fluids. Additionally in some instances, analyzing 150 the patient's response comprises repeating the steps of determining 120 the patient's tolerance and verifying 130 the patient's internal chemistry. In further instances, repeating these steps comprises providing 170 a first feedback for the present method.

Adjusting 160 the concentration of the cocrystalline formulation comprises adjusting the concentration that is administered to the patient in order to improve the condition. Additionally, adjusting 160 the concentration is to account for changes in the patient's tolerance (see e.g. determining 120 the patient's tolerance), internal chemistry (see e.g. verifying 130 the patient's internal chemistry), and in certain instances changing the concentration provided to the patient (see e.g. providing 140 a concentration of a cocrystalline formulation). In further instances, repeating these steps comprises providing 180 a second feedback for the present method.

FORMULATION. Generally, the DHEA cocrystalline formulations of the present disclosure comprise at least about 50 mg of the DHEA cocrystal. In some instances, the disclosed formulations comprise at least about 250 mg and alternatively, at least about 1000 mg of the DHEA cocrystal. The DHEA cocrystalline formulations comprise a stoichiometric ratio of the DHEA and the coformer. Further, the stoichiometric ratio is the molar ratio of DHEA to coformer. As described herein the molar ratio of DHEA to the coformer is any molar ratio ranging from about 1:100 to about 100:1. In certain formulations, the molar ratios of the present disclosure are approximately equimolar, having a molar ratio of DHEA to coformer of approximately 1:1. The DHEA cocrystalline formulations having this stoichiometric ratio are prepared to achieve at least a 50% yield from the reactants and, alternatively, the cocrystalline formulations are prepared to achieve at least a 70% yield from the reactants in this stoichiometric ratio.

The DHEA cocrystalline formulations disclosed herein are analyzed to confirm the quantity, quality, the purity, or combinations thereof. In instances, each of the compounds and the cocrystalline formulation is confirmed by x-ray diffraction (XRD), x-ray powder diffraction (XRPD), differential scanning calorimetry (DSC), thermo-gravimetric analysis (TG), nuclear magnetic resonance (NMR), Raman spectroscopy (RS), dissolution testing (DT), or combinations thereof.

In certain instances, the cocrystalline formulation analysis comprises determining the dissolution of the DHEA cocrystalline formulations by dissolution testing (DT). The analysis of a DHEA cocrystalline formulation dissolution is conducted by stirring the formulation in an aqueous bath for a predetermined time. In instances, the aqueous solution comprises a water or aqueous solution. Generally, the aqueous solution comprises inorganic and ionic compounds such as salts, minerals, or electrolytes without limitation. Further, in certain analyses the water or aqueous solution has a pH between about pH 5 and about pH 9, alternatively between about pH 6 and about pH 8. The water-based solution is considered an in vitro environment for the dissolution of the cocrystals. For example, the water or aqueous solution is a simulated subcutaneous, intravenous, intramuscular, oral, cardiovascular, respiratory, or digestive environment, without limitation. The dissolution analysis relates to the time to convert the DHEA co-crystals to solid DHEA as aqueous slurry.

DHEA and GLUTARIC ACID. Glutaric acid as used herein refers to any pentanedioic acid, including propane-1,3-dicarboxylic acid, 1,3-propanedicarboxylic acid, n-pyrotartaric acid, and others without limitation by theory or naming convention. Generally, the DHEA/glutaric acid co-crystal is formed by solvent evaporation. The evaporation conditions and solvent are any suitable to form a DHEA/glutaric acid co-crystal. In certain instances, a DHEA/glutaric acid co-crystal is formed by rotary evaporation of the solvent acetone at approximately 60° C. Further, the rotary evaporation to form DHEA/glutaric acid co-crystals is conducted until at least an approximately 75% yield of the DHEA/glutaric acid co-crystal is reached from the individual compounds.

DHEA and MALEIC ACID. Maleic acid as used herein refers to any butenedoic acid, including Z-butenedoic acid, monounsaturated cis-dicarboxylic-acid, malenic acid, maleinic acid, toxilic acid, and others without limitation by theory or naming convention. Generally the DHEA/maleic acid co-crystal is formed by solvent evaporation. The evaporation conditions and solvent are any suitable to form a DHEA/maleic acid co-crystal. In certain instances, a DHEA/maleic acid co-crystal is formed by rotary evaporation of the solvent acetone at approximately 60° C. Further, the rotary evaporation to form DHEA/maleic acid co-crystals is conducted until at least an approximately 75% yield of the DHEA/maleic acid co-crystal is reached from the individual compounds.

DHEA and TARTARIC ACID. Tartaric acid as used herein refers to any dextrotartaric acid, including thearic acid, racemic acid, uvic acid, paratartaric acid, 2,3-dihydroxybutanedioic acid, 2,3-dihydroxysuccinic acid, and others without limitation by theory or naming convention. Further, tartaric acid as used herein relates to a homochiral or an enantiopure compound of the L-isomer chiral molecule. Generally, the DHEA/tartaric acid co-crystal is formed by solvent evaporation. The evaporation conditions and solvent are any suitable to form a DHEA/tartaric acid co-crystal. In certain instances, a DHEA/tartaric acid co-crystal is formed from a solvent slurry of the tartaric acid. In instances, the solvent slurry comprises a volume ratio of 1:2 of the solvents tetrahydrofuran:heptane. The tartaric acid is dissolved in the solvent mixture and DHEA is added until a solid persists. Subsequently, additional solvent or DHEA is added under stirring at ambient temperatures. The resulting slurry is centrifuged, filtered, or dried to form the DHEA/tartaric acid cocrystal as a solid. In further instances, the DHEA/tartaric acid co-crystal is dried at approximately 60° C. Further, the rotary evaporation to form DHEA/tartaric acid co-crystals is conducted until at least an approximately 75% yield of the DHEA/tartaric acid co-crystal is reached from the individual compounds.

DHEA and FRUCTOSE. Fructose as used herein refers to any generically named fruit sugar, including levulose, D-fructopyranose, D-fructofuranose, D-arabino-hexulose, fructan-monomer, and others without limitation by theory or naming convention. Further, fructose as used herein relates to the homochiral or the enantiopure compound of the D-isomer chiral molecule. Generally, the DHEA/fructose co-crystal is formed by melt-cooling crystallization. The cooling conditions are any suitable to form a DHEA/fructose co-crystal. In instances, a DHEA/fructose co-crystal is formed by melting DHEA in contact with fructose. In certain instances, the DHEA and fructose solids are heated to a temperature of approximately 155° C. Crystallization occurred by permitting the melted DHEA and fructose to cool. In certain instances, the DHEA/fructose co-crystal is formed by cooling the DHEA and fructose melt to ambient temperatures. Alternatively, partially cooling the DHEA and fructose melt to approximately 135° C., before the melt is seeded with previous DHEA/fructose co-crystals. In some instances, the seeding temperature is less than about 90% of the melting temperature for DHEA in contact with fructose. Further, the melt-cooling crystallization, including seeded cooling, to form DHEA/fructose co-crystals is conducted until at least an approximately 50% yield of the DHEA/fructose co-crystal is reached from the individual compounds.

In further formulations of the present disclosure, the DHEA cocrystalline formulation further comprises an excipient or carrier. The excipient is an additive that stabilizes a solution of the cocrystalline formulation at a high supersaturation level long enough to allow absorption. Stabilizing the solution increases the concentration of the DHEA cocrystalline formulation in a solution. In the formulations of the present disclosure, the excipients comprise a concentration between about 0.01% by weight (wt %) to about 10% by weight (wt %) of the DHEA cocrystalline formulation. In some instances, the excipients comprise a concentration between about 0.5 wt % and about 5 wt % or alternatively, between about 0.5 wt % and about 2.5 wt % of the DHEA cocrystalline formulation. In exemplary concentrations, the excipient comprises about 1 wt % of the DHEA cocrystalline formulation.

Generally, the excipient is a biologically inert polymer that delays precipitation of the API from an aqueous solution. Non-limiting exemplary excipients include polyethylene glycol (PEG), poly-vinylpyrrolidone (PVP), vinylpyrrolidone-vinylacetate copolymer (e.g. PLASDONE S-630), and polyoxyethylene-sorbitan-mono-oleate ester (e.g. POLYSORBATE 80). In the present formulations, the excipients increase the concentration of DHEA cocrystalline formulation in an aqueous solution over time. More specifically, the excipients in a DHEA cocrystalline formulation maintain supersaturation of an aqueous solution. In instances, the DHEA cocrystalline formulation concentration in aqueous solutions exceeds about 50 μg/ml (mass/volume); the concentration exceeds about 120 μg/ml; and in certain instances, the concentration of the DHEA cocrystalline formulation in an aqueous solution exceeds about 236 μg/ml. Further, the excipients used herein maintain the supersaturation of the aqueous solution for at least about 60 minutes; in certain formulations for at least about 120 minutes; and in still further alternative formulation, for at least about 240 minutes.

To further illustrate various exemplary embodiments of the present invention, the following examples are provided.

EXAMPLES

Preparation of Cocrystals.

Four cocrystals were prepared in large enough quantities to be used in dissolution studies as shown in FIG. 4. Eight separate experiments are represented.

Figure 5:
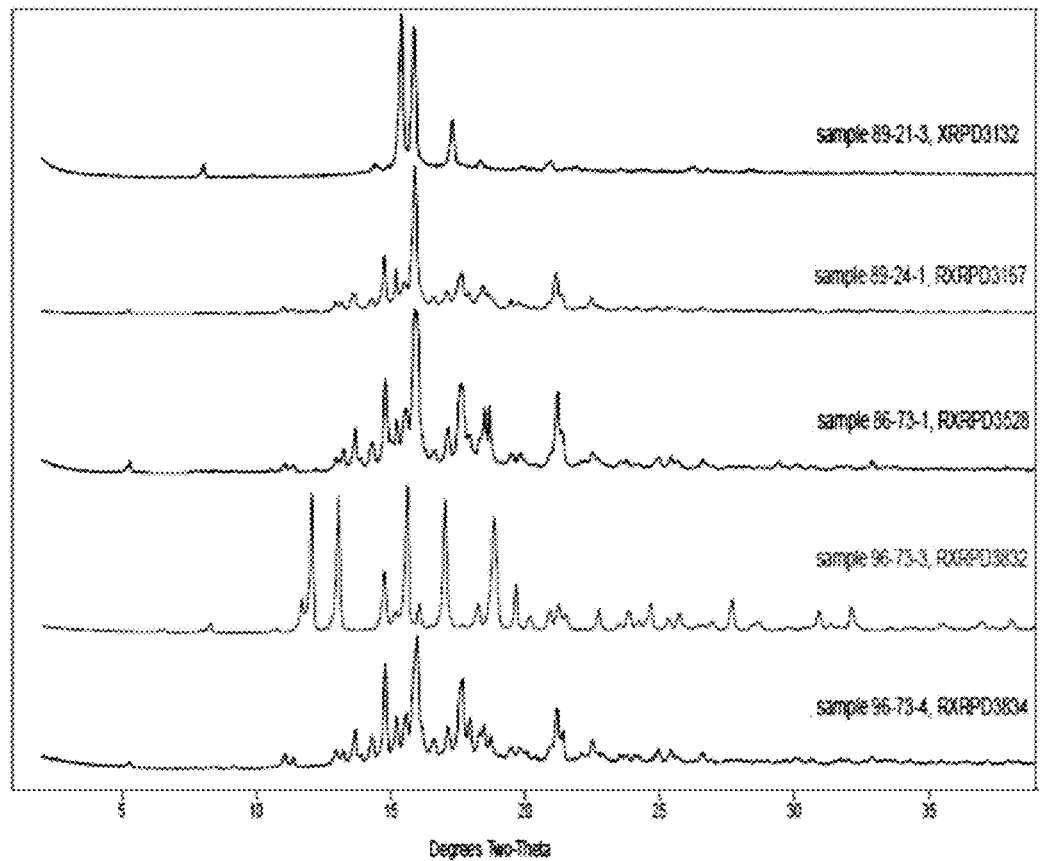
FIG. 5 illustrates a graphical overlay plot of X-ray powder diffraction ("XRPD") patterns from samples of the DHEA/D-fructose cocrystalline formulations according to an exemplary embodiment of the present disclosure.

The DHEA/D-fructose cocrystal was made by cooling melts containing equimolar amounts of the components. In one of three preparations the product exhibited a previously-unseen XRPD pattern (sample 96-73-3). The nature of that material is unknown but suggests that the DHEA/D-fructose cocrystal is polymorphic. Two solid forms of the cocrystal (1 and 2) were seen during the screening project. Material exhibiting the new pattern (sample 96-73-3) was designated form 3. The two samples exhibiting XRPD patterns of polymorph 1 and 2, were used in the dissolution studies. An overlay plot of XRPD patterns from samples of the DHEA/D-fructose cocrystal is shown in FIG. 5.

Figure 6:
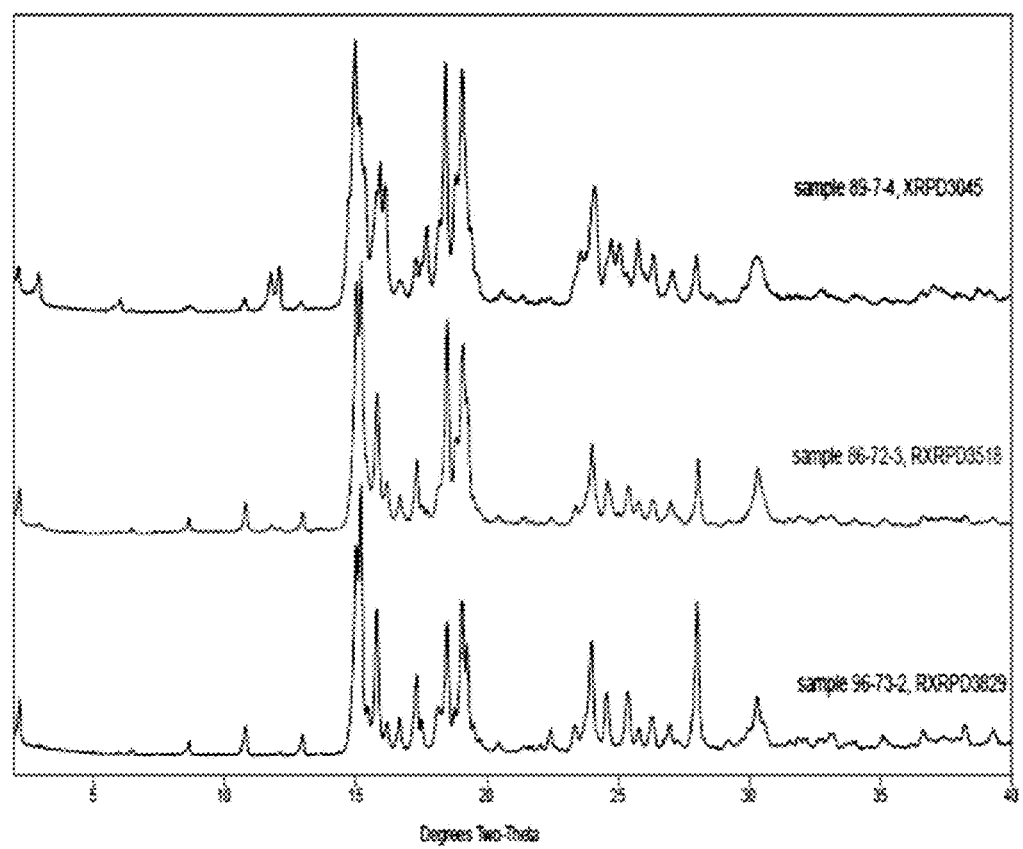
FIG. 6 illustrates a graphical overlay plot of XRPD patterns from samples of the DHEA/maleic acid cocrystalline formulations according to an exemplary embodiment of the present disclosure.
Figure 7:
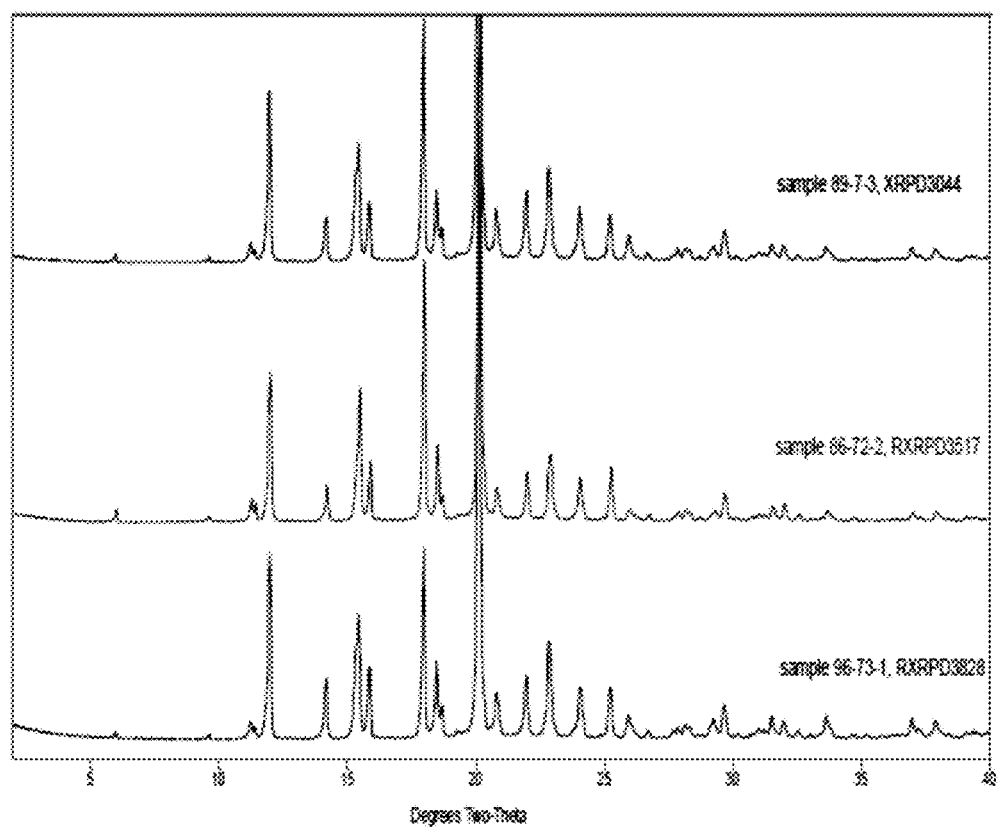
FIG. 7 illustrates a graphical overlay plot of XRPD patterns from samples of the DHEA/glutaric acid cocrystalline formulations according to an exemplary embodiment of the present disclosure.

The DHEA/maleic acid and DHEA/glutaric acid cocrystalline formulations were made by rapid evaporation of solvent from solutions containing equimolar amounts of the components. The samples prepared exhibited the XRPD patterns as shown in FIG. 6 and FIG. 7, respectively.

Figure 8:
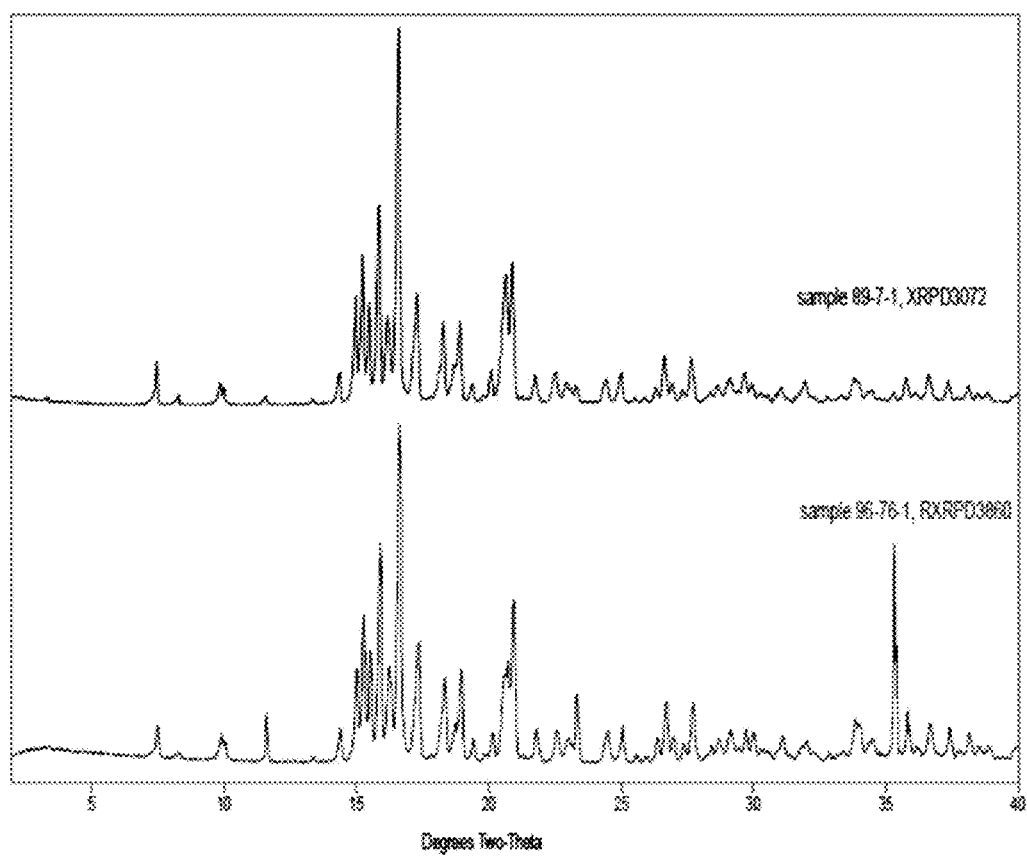
FIG. 8 illustrates a graphical overlay plot of XRPD patterns from samples of the DHEA/L-tartaric acid cocrystalline formulations according to an exemplary embodiment of the present disclosure.

The DHEA/L-tartaric acid cocrystalline formulation was prepared by generating a slurry of an equimolar mixture of the solid components in solvent saturated with each component. Initially the crystallization did not go to completion, so a third experiment was seeded with the cocrystal to produce the desired cocrystalline formulation product. The sample exhibited an XRPD pattern shown in FIG. 8.

Methods.

X-ray Powder Diffraction (XRPD): The Rigaku Smart-Lab X-ray diffraction system was configured for reflection Bragg-Brentano geometry using a line source X-ray beam. The x-ray source is a Cu Long Fine Focus tube that was operated at 40 kV and 44 mA. This source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1 °2θ or less. The axial divergence of the X-ray beam is controlled by 5.0-degree Soller slits in both the incident and diffracted beam paths.

Powder samples were prepared in a low background Si holder using light manual pressure to keep the sample surfaces flat and level with the reference surface of the sample holder. The single-crystal, Si, low-background holder has a small circular recess (7 mm diameter and about 1 mm depth) that holds between 5 and 10 mg of powdered material. Each sample was analyzed from 2 to 40 °2θ using a continuous scan of 6 °2θ per minute with an effective step size of 0.02 °2θ.

High performance liquid chromatography (HPLC) analyses were carried out on an Agilent 1100 series instrument equipped with a UV detector using the following materials and operating parameters:

| | |
|---|---|
| column | YMC C18, 4.6 × 250 mm, 3 μm |
| detector wavelength | 292 nm |
| mobile phase | acetonitrile |
| injection volume | 40 μL |
| flow rate | 1.0 mL/min |
| run time | 8 min |

The retention time of the DHEA peak was about 4.7 min. Calibration data used previously and standards analyzed prior to the samples were used to generate concentrations from peak areas.

Simulated intestinal fluid (SIF) was prepared by dissolving 21.6 mg of sodium hydroxide, 168.8 mg of sodium dihydrogen phosphate dihydrate, 311.6 mg of sodium chloride, and 113.0 mg of SIF Powder Original (Biorelevant) in 50 mL of water. A 100-mL, round-bottom flask was charged with 10 mL of SIF and a stir bar. The flask was placed in a 37° C. bath and stirring was begun. A 20-mL vial was charged with 10 mL of water and placed in a 37° C. bath.

Preparation of DHEA/D-Fructose Cocrystal (sample 86-73-1): A mixture of 105.0 mg (0.364 mmol) of DHEA (sample TL876) and 65.9 mg (0.366 mmol) of D-fructose was placed in a vial. The vial was placed in an oil bath and heated until the solid melted (155° C.). The mixture was allowed to cool to room temperature, during which time crystallization occurred. When the sample reached ambient temperature it was removed from the vial with a spatula to give 87.4 mg (51% yield) of DHEA/D-fructose cocrystal (sample 86-73-1). That sample was analyzed by XRPD, which indicated it was form 1.

Preparation of DHEA/D-Fructose Cocrystal (sample 96-73-3): A mixture of 220.6 mg (0.765 mmol) of DHEA (sample TL876) and 136.8 mg (0.759 mmol) of D-fructose was placed in a vial. The vial was placed in an oil bath and heated until the solid melted (155° C.). The mixture was allowed to cool to room temperature, during which time crystallization occurred. When the sample reached ambient temperature it was placed in a vial (sample 96-73-3) and analyzed by XRPD, which indicated it was a previously-unseen solid form.

Preparation of DHEA/D-Fructose Cocrystal (sample 96-73-4): A mixture of 133.5 mg (0.463 mmol) of DHEA (sample TL876) and 84.1 mg (0.467 mmol) of D-fructose was placed in a vial. The vial was placed in an oil bath and heated until the solid melted (155° C.). The mixture was allowed to cool to 135° C., during which time it remained a clear liquid, and seeded with a small amount of sample 86-73-1. Crystallization occurred quickly. The sample was allowed to cool to ambient temperature, placed in a vial (sample 96-73-4) and analyzed by XRPD, which indicated it was form 1.

Preparation of the DHEA/Glutaric Acid Cocrystal (sample 86-72-2): A solution of 109.9 mg (0.381 mmol) of DHEA (sample TL876) and 50.2 mg (0.380 mmol) of glutaric acid in about 4 mL of acetone was concentrated on a rotary evaporator at 60° C. The resulting white solid was recovered to give 151.5 mg (95% yield) of the DHEA.glutaric acid cocrystal (sample 86-72-2).

Preparation of the DHEA/Glutaric Acid Cocrystal (sample 96-73-1): A solution of 277.3 mg (0.961 mmol) of DHEA (sample TL876) and 127.0 mg (0.961 mmol) of glutaric acid in about 7 mL of acetone was concentrated on a rotary evaporator at 60° C. The resulting white solid was recovered to give the DHEA/glutaric acid cocrystal (sample 96-73-1), which was analyzed by XRPD.

Preparation of the DHEA/Maleic Acid Cocrystal (sample 86-72-3): A solution of 124.2 mg (0.431 mmol) of DHEA (sample TL876) and 50.5 mg (0.435 mmol) of maleic acid in about 4 mL of acetone was concentrated on a rotary evaporator at 60° C. The resulting white solid was recovered to give 159.5 mg (91% yield) of the DHEA/maleic acid cocrystal (sample 86-72-3).

Preparation of the DHEA/Maleic Acid Cocrystal (sample 96-73-2): A solution of 273.4 mg (0.948 mmol) of DHEA (sample TL876) and 11.0 mg (0.956 mmol) of maleic acid in about 7 mL of acetone was concentrated on a rotary evaporator at 60° C. The resulting white solid was recovered to give the DHEA/maleic acid cocrystal (sample 96-73-2), which was analyzed by XRPD.

Preparation of the DHEA/L-Tartaric Acid Cocrystal (sample 86-72-1): Portions of L-tartaric acid were added to 1.2 mL of a 1:2 mixture of tetrahydrofuran:heptane at ambient temperature until solid persisted. The resulting slurry was stirred for 1 hour at ambient temperature and treated with one portion of DHEA (TL876). The resulting slurry was stirred at ambient temperature for 4 hours. The slurry was centrifuged. The liquid portion was placed in a vial and treated with 84.8 mg (0.294 mmol) of DHEA (sample TL876) and 44.2 mg (0.294 mmol) of L-tartaric acid. The resulting slurry was stirred at ambient temperature overnight and centrifuged. The liquid was removed by decantation and the solid was dried in an oven at 60° C. for a few minutes. The solid (sample 86-72-1) was found to be DHEA form I by XRPD analysis.

Preparation of the DHEA/L-Tartaric Acid Cocrystal (sample 86-78-1): Portions of L-tartaric acid were added to 1.2 mL of a 1:2 mixture of tetrahydrofuran:heptane at ambient temperature until solid persisted. The resulting slurry was stirred for 4 hours at ambient temperature and treated with one portion of DHEA (TL876). The resulting slurry was stirred at ambient temperature overnight and vacuum filtered. The solid (sample 86-78-1) was found to be a mixture of DHEA and the DHEA/L-tartaric acid cocrystal by XRPD analysis.

Preparation of the DHEA/L-Tartaric Acid Cocrystal (sample 96-76-1): Portions of L-tartaric acid were added to 1 mL of a 1:2 mixture of tetrahydrofuran:heptane at ambient temperature until solid persisted. The resulting slurry was stirred for 15 minutes at ambient temperature and treated portion wise with DHEA (TL876) until solid DHEA persisted (judged by visual inspection). The slurry was stirred at ambient temperature for 40 minutes and seeded with a small amount of DHEA/L-tartaric acid cocrystal (sample 89-7-1). The resulting slurry was stirred at ambient temperature for 15 minutes, during which time it thickened. It was treated with 1 mL of a 1:2 mixture of tetrahydrofuran:heptane to thin the slurry and, after thickening again over 85 minutes, was treated with another 1 mL portion of that solvent. The slurry was centrifuged and the liquid was removed by decantation. The decantate was treated with 129.9 mg of DHEA (0.450 mmol) of DHEA (sample TL876) and 68.1 mg (0.454 mmol) of L-tartaric acid. The resulting slurry was stirred at ambient temperature overnight and vacuum filtered to give 176.0 mg (89% yield) of the DHEA/L-tartaric acid cocrystal (sample 96-76-1), which was analyzed by XRPD.

An aqueous solution of pH 6.8 buffer was made by dissolving 339.6 mg of potassium dihydrogen phosphate and 11.2 mL of 0.1 M NaOH in 50 mL of water. A slurry of 28.8 mg of the DHEA/D-fructose cocrystal in 5 mL of the pH 6.8 buffer solution was stirred at ambient temperature. At selected time points (10 minutes, 30 minutes, 1 hour, 2 hours, and 5 hours) the slurry was centrifuged and 700 μL of the liquid phase was withdrawn and passed through a 0.5 μm PTFE filter. The filtrate was concentrated in a purge of dry air until all the water evaporated, leaving a solid that was analyzed by HPLC. At 22 hours the slurry was vacuum filtered. The pH of the filtrate was measured using a Thermo Scientific Orion 3 Star pH meter. The collected solid was analyzed by XRPD. The filtrate was concentrated in a purge of dry air until all the water evaporated, leaving a solid that was analyzed by HPLC.

Dissolution.

Initial dissolution was carried out to estimate the time necessary for conversion of the cocrstals to DHEA in aqueous slurries. The results are shown in FIG. 9. The DHEA/L-tartaric acid cocrystal appears to convert very quickly. The DHEA/glutaric acid and DHEA/maleic acid cocrystals appear to convert more slowly, as mixtures of DHEA and cocrystals seem to be present in the solid phases after stirring in water overnight. The XRPD pattern exhibited by the solid obtained on stirring the DHEA/D-fructose cocrystal in water overnight did not match any of the relevant patterns.

Further dissolution studies with concentration measurements at 10 minutes, 30 minutes, 1 hour, 2 hours, 5 hours, and overnight were conducted. Three such experiments were carried out, using DHEA polymorph form I (FI), the DHEA/D-fructose cocrystal, and the DHEA/glutaric acid cocrystal. The data were very similar within the experiments and specifically, there was no change in concentration of DHEA with time and the remaining solids were DHEA form S2 (monohydrate). Thus, the cocrystal conversion to DHEA occurs very quickly and additional dissolution data were collected for DHEA and all cocrystals at time points shorter than 10 minutes. All of the data are summarized in FIG. 10 through FIG. 14 and the data are plotted in FIG. 15 through FIG. 19.

Figure 15:
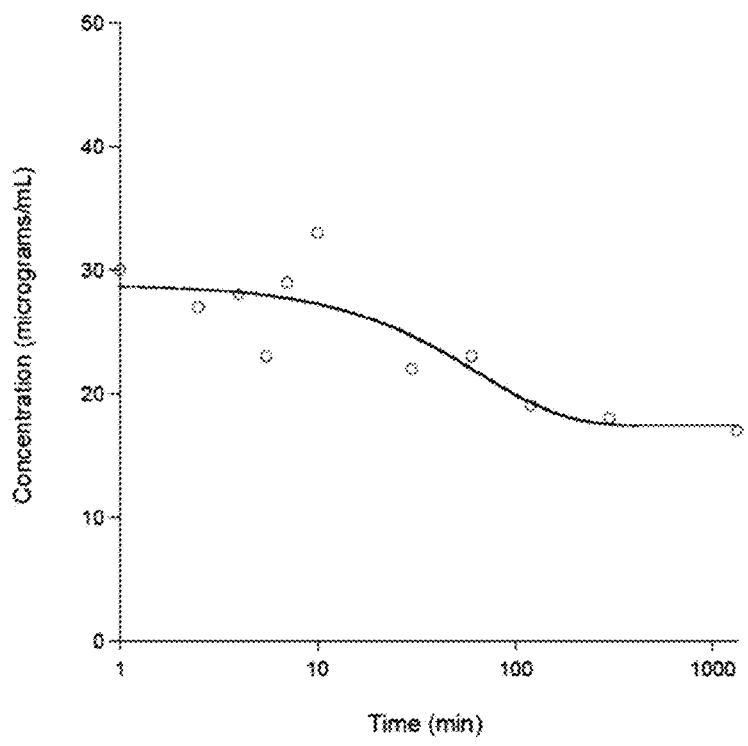
FIG. 15 illustrates a dissolution curve for DHEA polymorph form I (FI) over a logarithmic time scale according to an exemplary embodiment of the present disclosure.
Figure 16:
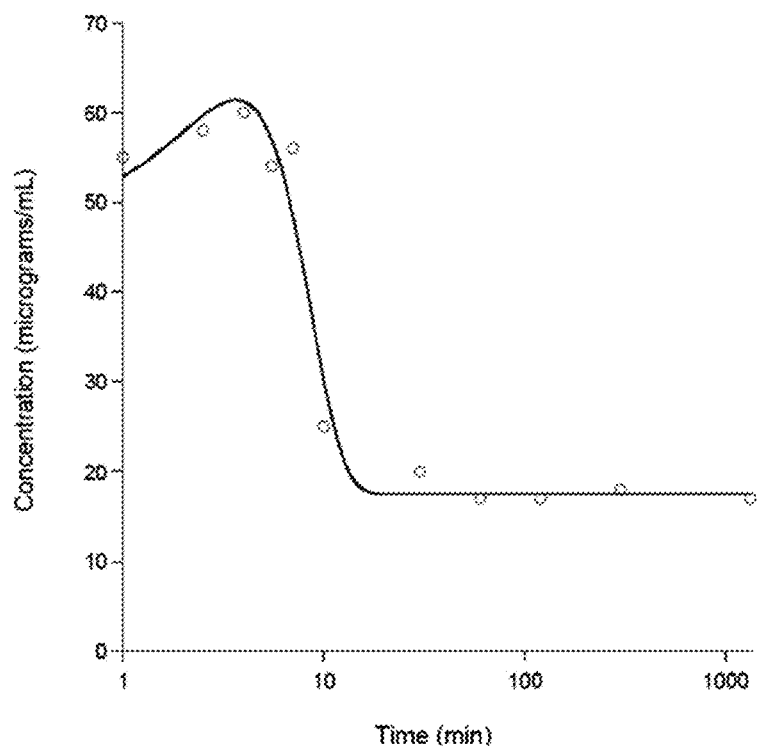
FIG. 16 illustrates a dissolution curve for DHEA/D-fructose cocrystalline formulation over a logarithmic time scale according to an exemplary embodiment of the present disclosure.
Figure 17:
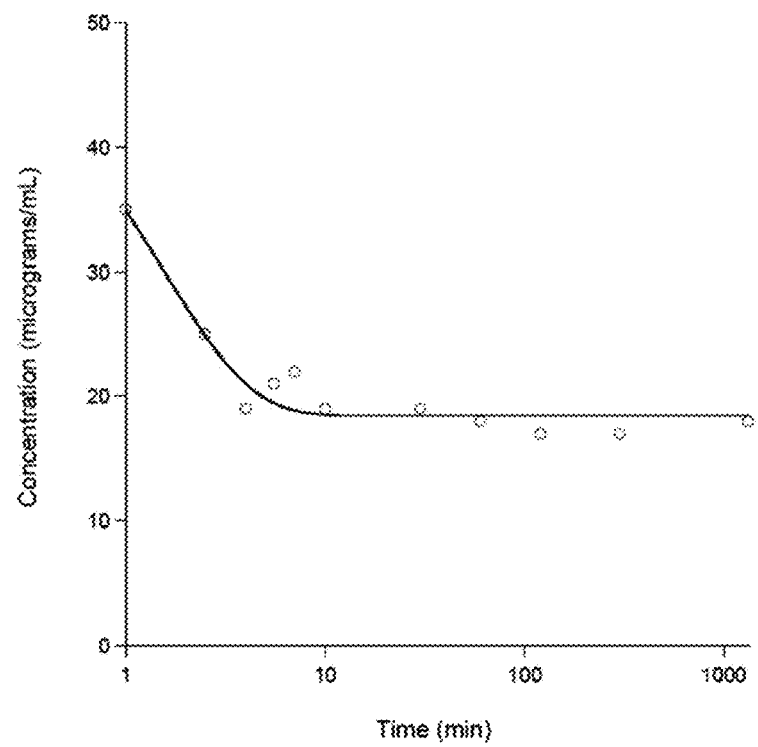
FIG. 17 illustrates a dissolution curve for DHEA/glutaric acid cocrystalline formulation over a logarithmic time scale according to an exemplary embodiment of the present disclosure.
Figure 18:
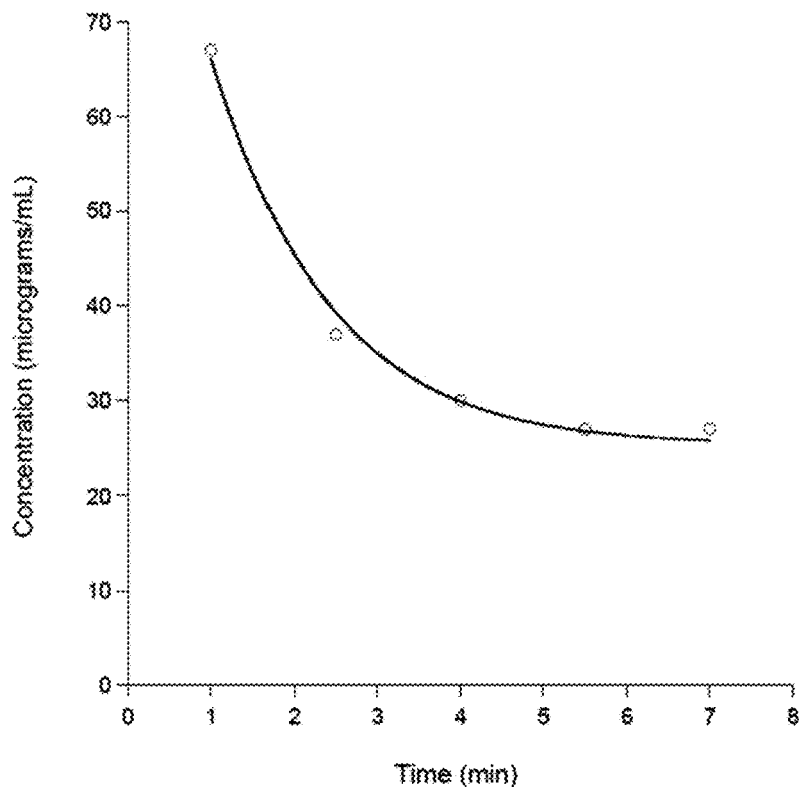
FIG. 18 illustrates a dissolution curve for DHEA/maleic acid cocrystalline formulation according to an exemplary embodiment of the present disclosure.
Figure 19:
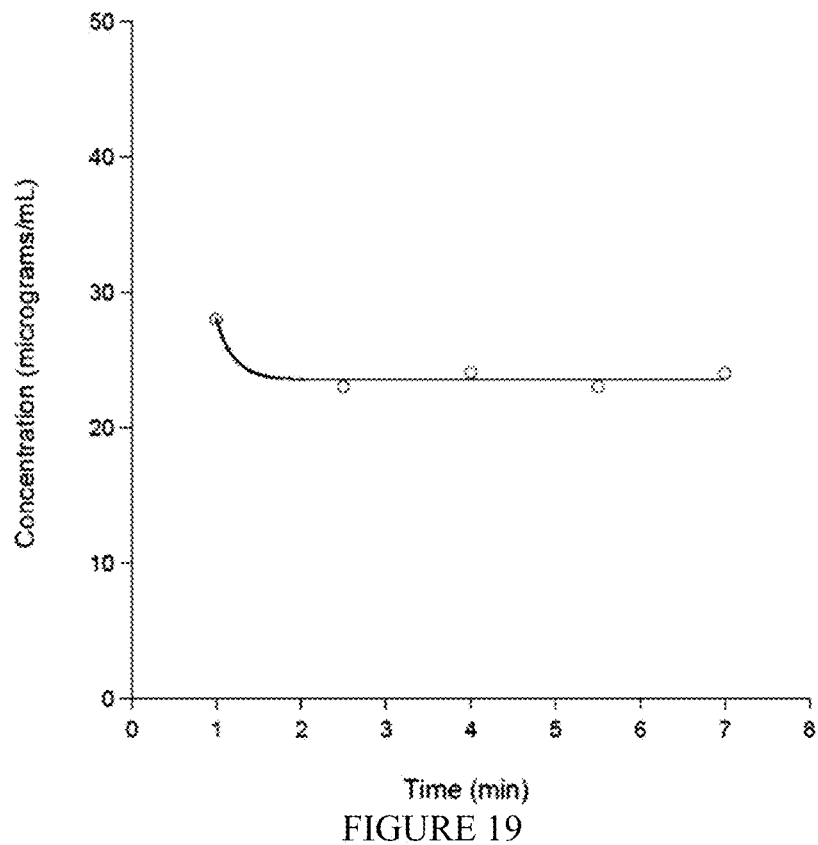
FIG. 19 illustrates a dissolution curve for DHEA/L-tartaric acid cocrystalline formulation according to an exemplary embodiment of the present disclosure.

Note that in each of the plots shown in FIGS. 9-11 the results of two experiments (time points at <10 min and time points at >10 minutes) are shown on one graph. In order to better visualize the curves, the x axes are in logarithmic scales (FIGS. 15-17). The tables shown in FIGS. 12 and 13 were derived from single experiments having time points at <10 minutes. The x axes on those plots are in linear scales (FIGS. 18 and 19).

The dissolution study starting with DHEA provided results that were within the calculated and theoretical expectations. A plot of the data in FIG. 15 shows that the solubility of the starting anhydrate form of DHEA (form FI) is about 30 µg/mL. That is supersaturated relative to the solubility of the monohydrate form of DHEA (form S1), which crystallizes from solution. The transformation of anhydrate to monohydrate is complete in about 2 hours. The solubility of the monohydrate is about 17 µg/mL.

A plot of the dissolution data from the experiment starting with the DHEA/D-fructose cocrystal is shown in FIG. 16. The curve displays the 'spring' delivered by the cocrystal, with the maximum concentration just above 60 µg/mL. That is about three times the solubility of DHEA itself. DHEA monohydrate, form S1, crystallizes from solution within 10 minutes and at the end of the experiment the DHEA concentration corresponds to the solubility of the monohydrate, about 17 µg/mL. The conversion of the DHEA/D-fructose cocrystal to DHEA monohydrate is faster than the conversion of DHEA anhydrate to monohydrate because of the greater supersaturation level obtained from the cocrystal.

A plot of the dissolution data from the experiment starting with the DHEA/glutaric acid cocrystal is shown in FIG. 17. The highest concentration observed, 35 µg/mL, was at the first (1 minute) time point. The maximum concentration obtained appears to have been present prior to 1 minute. All that can be seen is the later portion of the 'spring' curve. Conversion to the monohydrate is complete by about 10 minutes.

A plot of the dissolution data from the experiment starting with the DHEA/maleic acid cocrystal is shown in FIG. 18; the maximum concentration obtained appears to have been present prior to the first sample withdrawal at 1 minute. Conversion to the monohydrate did not appear to be complete by 7 minutes as the solubility at that time point was about 27 µg/mL, which is higher than the solubility of the hydrate (about 17 µg/mL). The maximum concentration measured, 67 µg/mL, was at the first time point and was the highest concentration seen in any of the dissolution experiments. It is expected that the concentration at the apex of the 'spring' curve was higher still.

A plot of the dissolution data from the experiment starting with the DHEA/L-tartaric acid cocrystal is shown in FIG. 19. The maximum concentration measured was at the first time point (1 minute) but was only 28 µg/mL. Equilibrium was obtained by 2.5 minutes, the cocrystal converting to a solid that exhibited a previously-unseen XRPD pattern. Therefore, the nature of that solid is unknown. Note that the equilibrium solubility of that solid species is about 24 µg/mL.

Thus, high supersaturation levels obtained on initial dissolution of the cocrystal need to be maintained long enough for absorption to occur. Based on the dissolution results, either the DHEA/D-fructose cocrystal or the DHEA/maleic acid cocrystal will be implemented for in vivo studies. In either case, the cocrystal will include excipients such as crystallization inhibitors to extend the lifetime of the supersaturated conditions.

Excipients.

Figure 20:
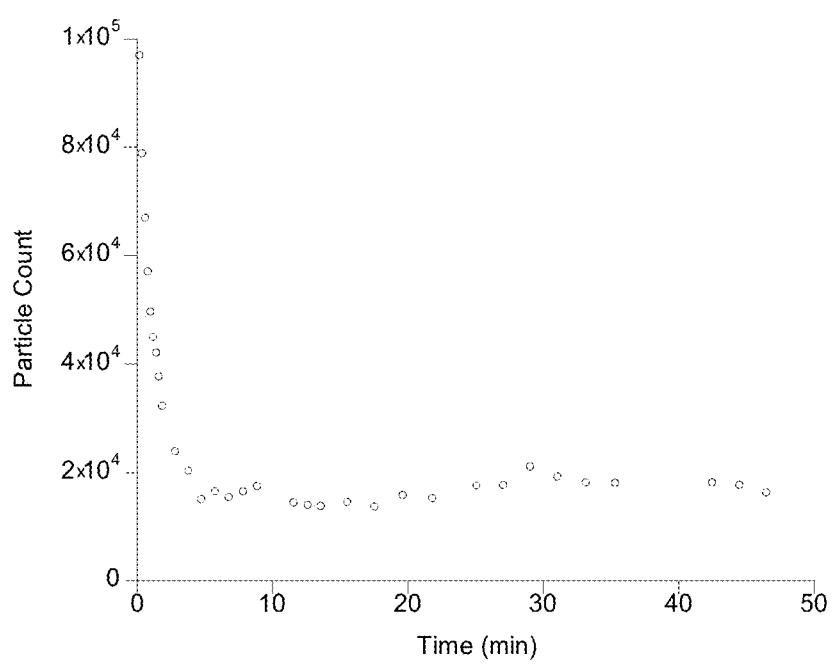
FIG. 20 illustrates particle count plot against time after DHEA addition to water to give a 32 µg/mL solution, to a 1.9× supersaturated state.
Figure 21:
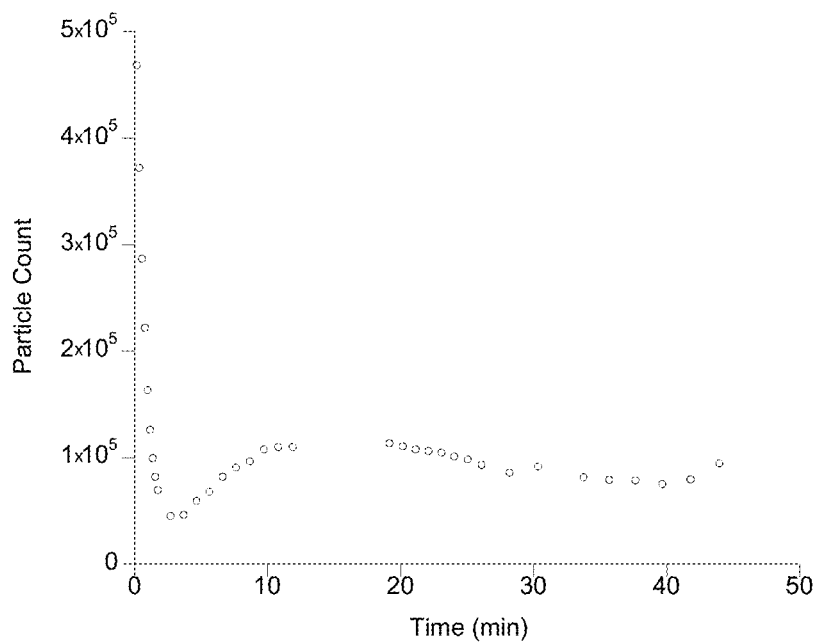
FIG. 21 illustrates particle count plot against time after DHEA addition to water to give a 48 µg/mL solution, to a 2.8× supersaturated state.
Figure 22:
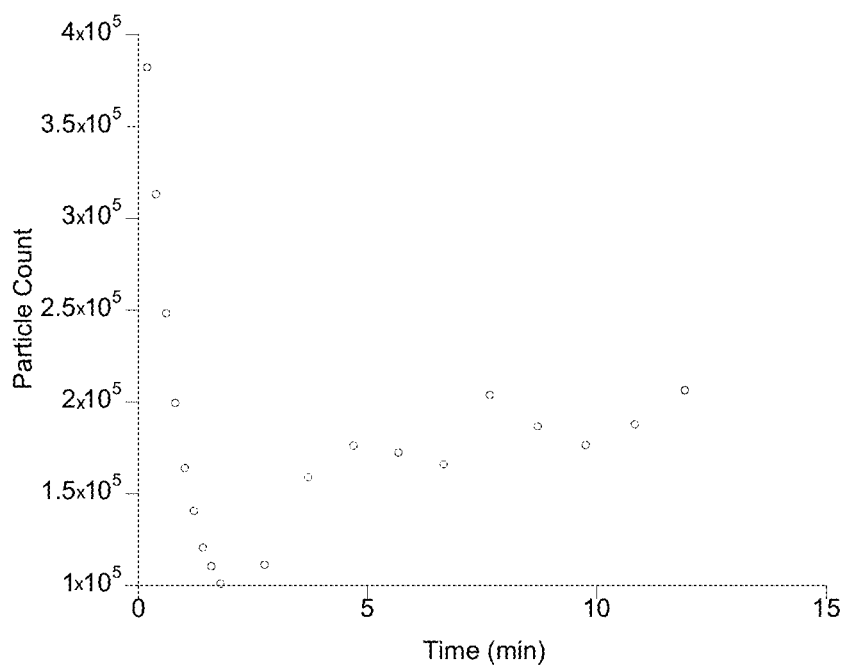
FIG. 22 illustrates particle count plot against time after DHEA addition to water to give a 64 µg/mL solution, to 3.8× supersaturated state.
Figure 64:
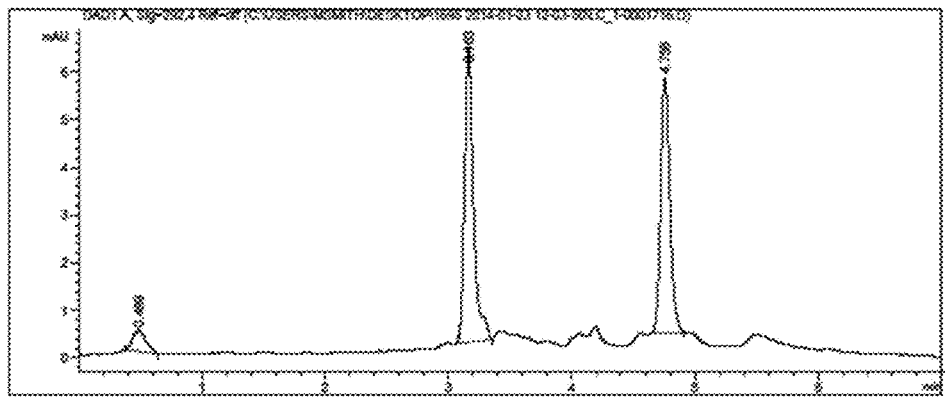
FIG. 64 illustrates a graph containing the data from HPLC 1716.
Figure 65:
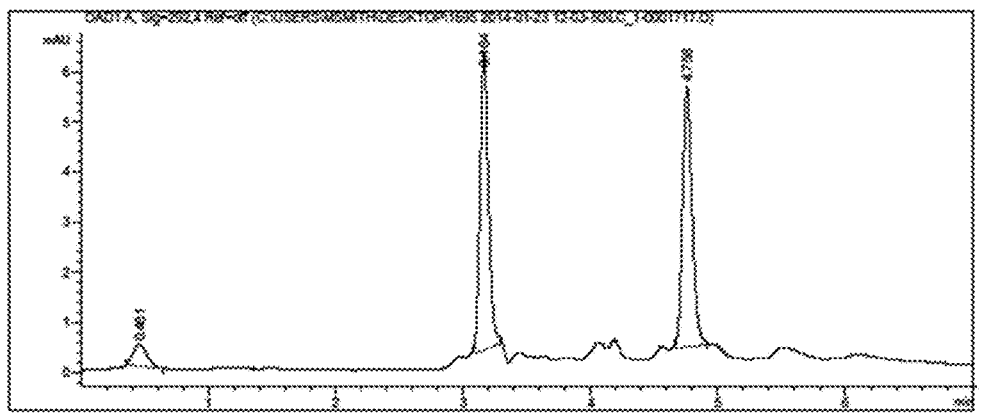
FIG. 65 illustrates a graph containing the data from HPLC 1717.
Figure 66:
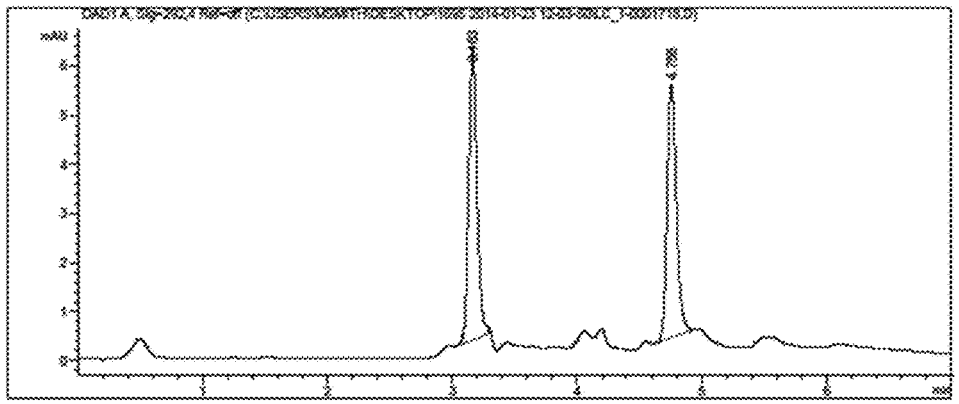
FIG. 66 illustrates a graph containing the data from HPLC 1718.
Figure 67:
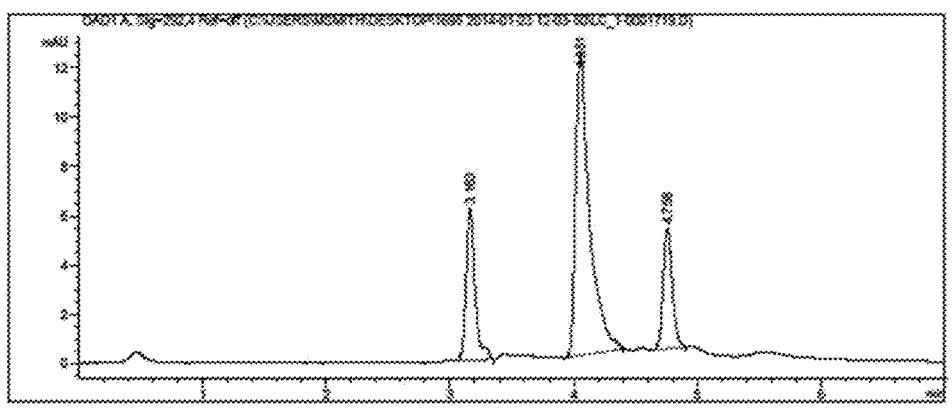
FIG. 67 illustrates a graph containing the data from HPLC 1719.
Figure 68:
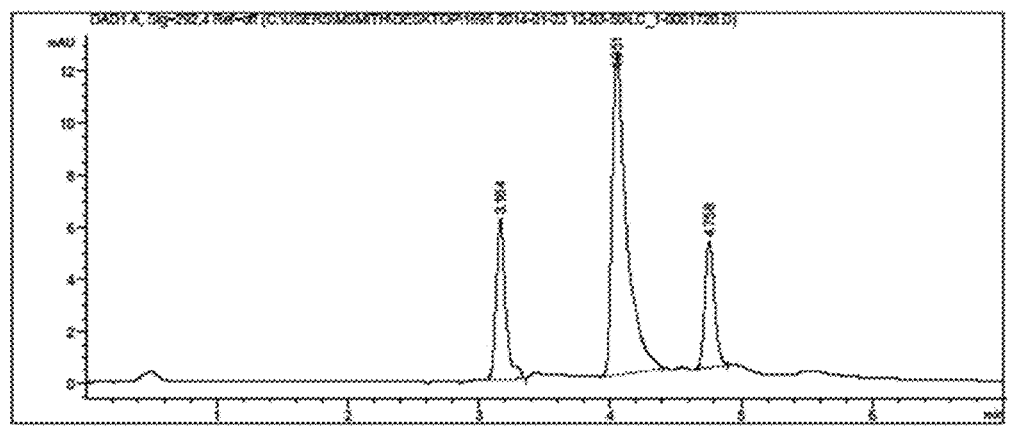
FIG. 68 illustrates a graph containing the data from HPLC 1720.

A method to create supersaturated solutions of DHEA in water was developed. The approach was to add concentrated solutions of DHEA in water-miscible organic solvents to water in amounts sufficient to create DHEA concentrations at supersaturation levels. The equilibrium solubility of DHEA hydrate S1, the most stable form in the presence of water, is 17 µg/ml. Experiments were conducted using a Hiac-Royco particle counter to measure the presence of solid particles in the mixtures. Initial experiments involved additions of single portions of a 64 µg/mL solution of DHEA in acetone to water. The amount of acetone solution added was varied to provide concentrations of 32 µg/mL (1.9× supersaturated) as shown in FIG. 20, 48 µg/mL (2.8× supersaturated) shown in FIG. 21, and 64 µg/mL (3.8× supersaturated) shown in FIG. 22. Total particle counts based on Hiac-Royco data were plotted against time after DHEA addition. The plots show that particle counts decrease with time. The fact that the largest particle count occurs at the shortest time suggests that solid DHEA separates from solution as soon as the aliquot of DHEA/acetone solution is added to water. Following that, particles probably ripen, replacing many small particles with fewer, larger ones. At the higher concentrations, particle counts decrease to a minimum and then increase slightly. That increase may represent conversion of an initially-precipitated DHEA form (perhaps an anhydrate) to less-soluble hydrate S1.

Figures 23, 24:
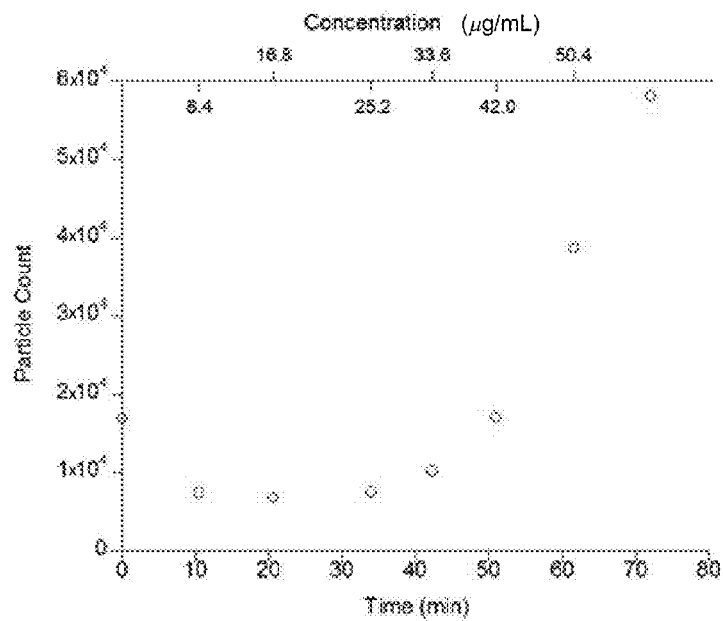
FIG. 23 illustrates a table of the excipients tested for use in a DHEA cocrystalline formulation according to an exemplary embodiment of the present disclosure.
FIG. 24 illustrates a graph of the supersaturated aqueous solutions that were generated by sequential additions of measured volumes of a 41.9 µg/mL solution of DHEA in DMF to 100 mL of water containing 1% of the PEG-6000.
Figure 25:
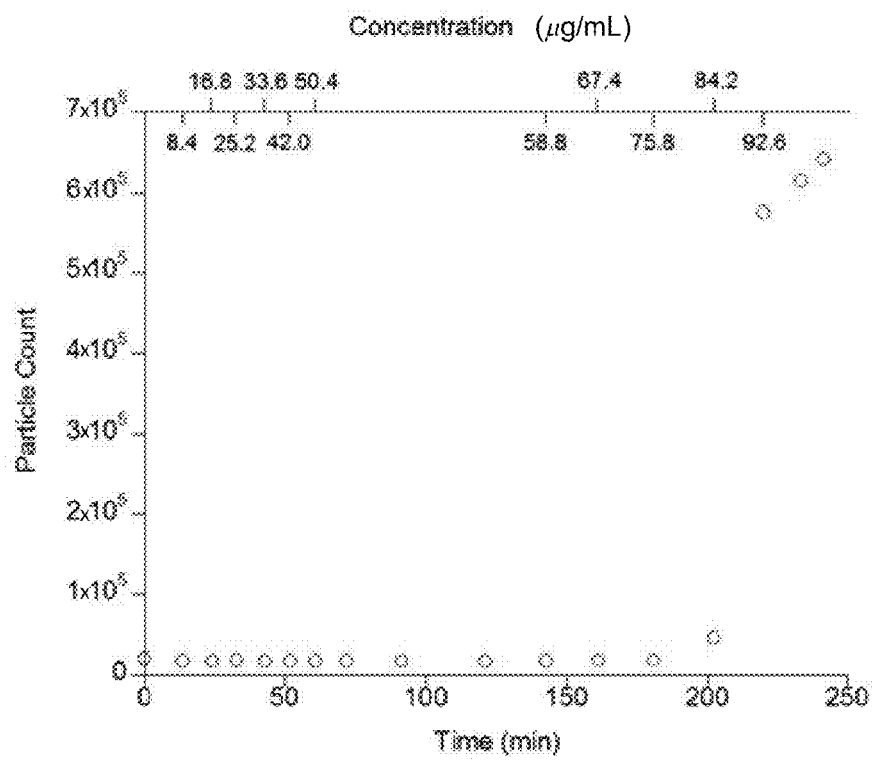
FIG. 25 illustrates a graph of illustrates a table of the supersaturated aqueous solutions were generated by sequential additions of measured volumes of a 41.9 µg/mL solution of DHEA in DMF to 100 mL of water containing 1% of the PLASDONE S-630.
Figure 26:
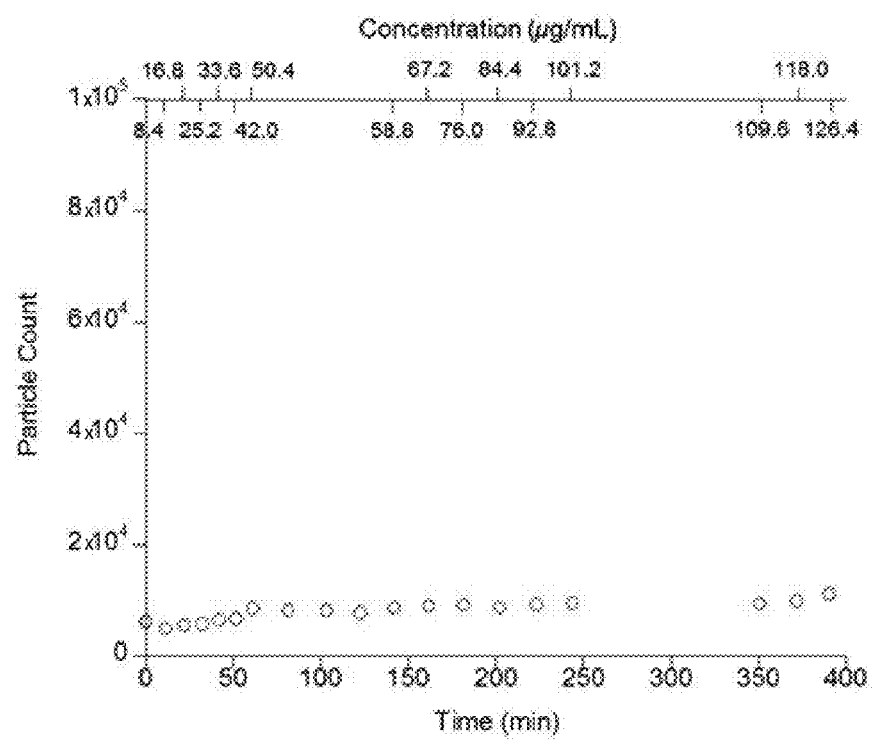
FIG. 26 illustrates a graph of the supersaturated aqueous solutions were generated by sequential additions of measured volumes of a 41.9 µg/mL solution of DHEA in DMF to 100 mL of water containing 1% of the POLYSORBATE 80.
Figure 27:
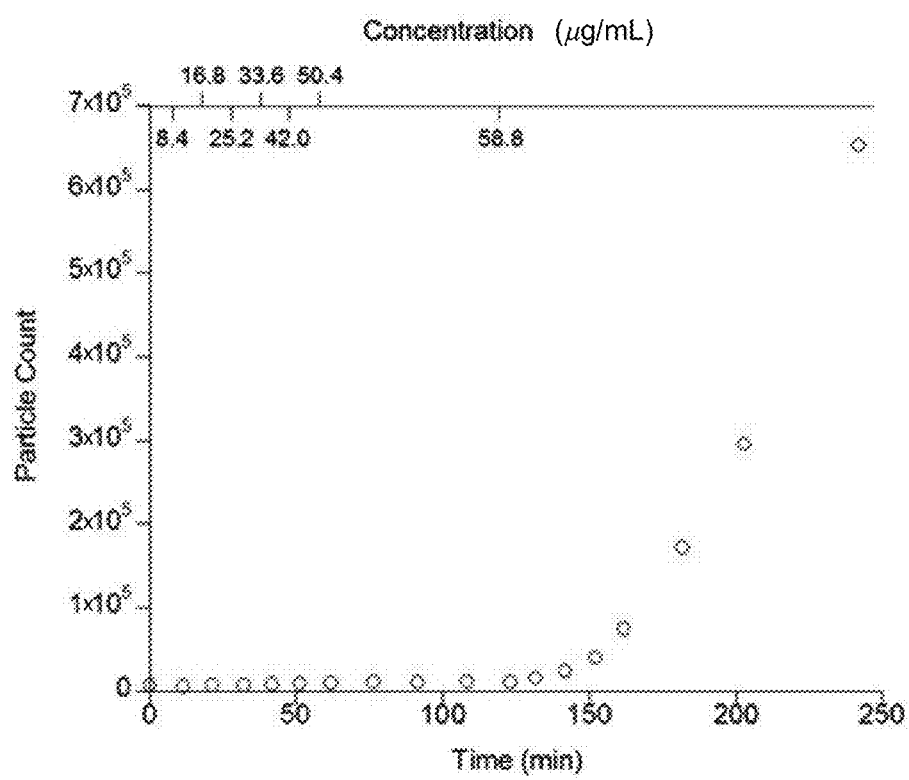
FIG. 27 illustrates a graph of the supersaturated aqueous solutions were generated by sequential additions of measured volumes of a 41.9 µg/mL solution of DHEA in DMF to 100 mL of water containing 1% of the PVP.

Subsequently the excipients were tested for their ability to delay or slow DHEA precipitation from supersaturated aqueous solutions by carrying out the same type of experiments described above using aqueous solutions of the test excipients in place of pure water. The excipients tested are listed in FIG. 23. Supersaturated aqueous solutions were generated by sequential additions of measured volumes of a 41.9 µg/mL solution of DHEA in DMF to 100 mL of water containing 1% of the test excipient and are shown in FIG. 24 through FIG. 27. Total particle counts based on Hiac-Royco data were plotted against time and DHEA concentration from the tables are illustrated in FIGS. 27-30. FIG. 24 shows that PEG-6000 has little effect on DHEA precipitation. The other three excipients tested inhibit precipitation as shown in FIG. 25 through FIG. 27. DHEA precipitated from the 1%

PVP solution at about 60 µg/mL, from 1% Plasdone S-630 solution at about 90 µg/mL, and did not precipitate from 1% Polysorbate 80 solution even at 126 µg/mL.

Based on the inhibitory effects found in the excipient screen, further studies with formulation slurries containing the cocrystals suspended in water were used, in which both Plasdone S-630 and Polysorbate 80 are dissolved. The formulation recipe and dissolution procedure are: bring 5 mL of simulated intestinal fluid (SIF) to 37° C., add about 6 mg of a cocrystal into 5 mL of water (at 37° C.) containing 2% Plasdone S630 and 1% Polysorbate 80 to give the formulation slurry, add the formulation slurry to the SIF, pull samples, filter, and analyze by HPLC. A control experiment was carried out in which DHEA was used instead of a cocrystal. The equilibrium solubility of DHEA (presumably hydrate S1) in this system is about 120-130 µg/mL.

Figure 28:
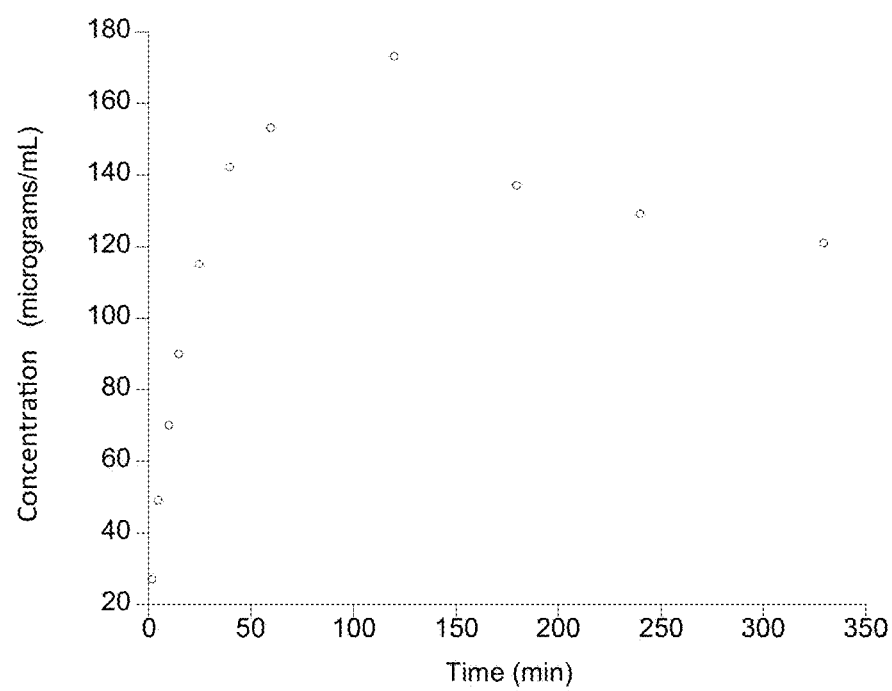
FIG. 28 illustrates a graph of the dissolution of formulated DHEA Form FI in simulated intestinal fluid.
Figure 29:
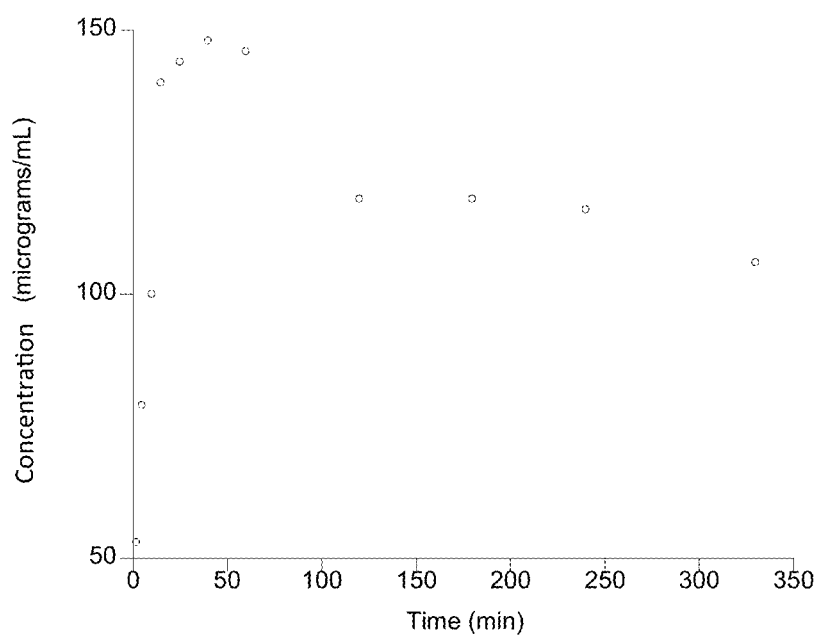
FIG. 29 illustrates a graph of the dissolution of a formulated DHEA/D-maleic acid cocrystal in simulated intestinal fluid.
Figure 30:
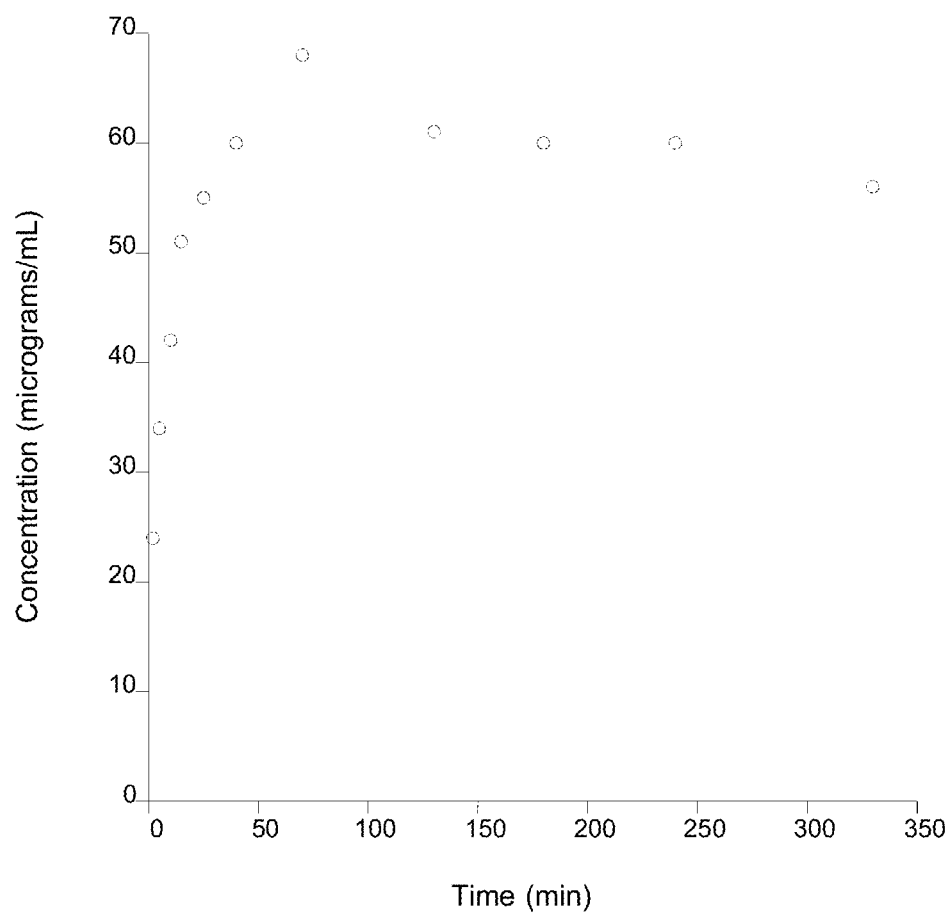
FIG. 30 illustrates a graph of the dissolution of unformulated DHEA Form FI in simulated intestinal fluid.
Figure 31:
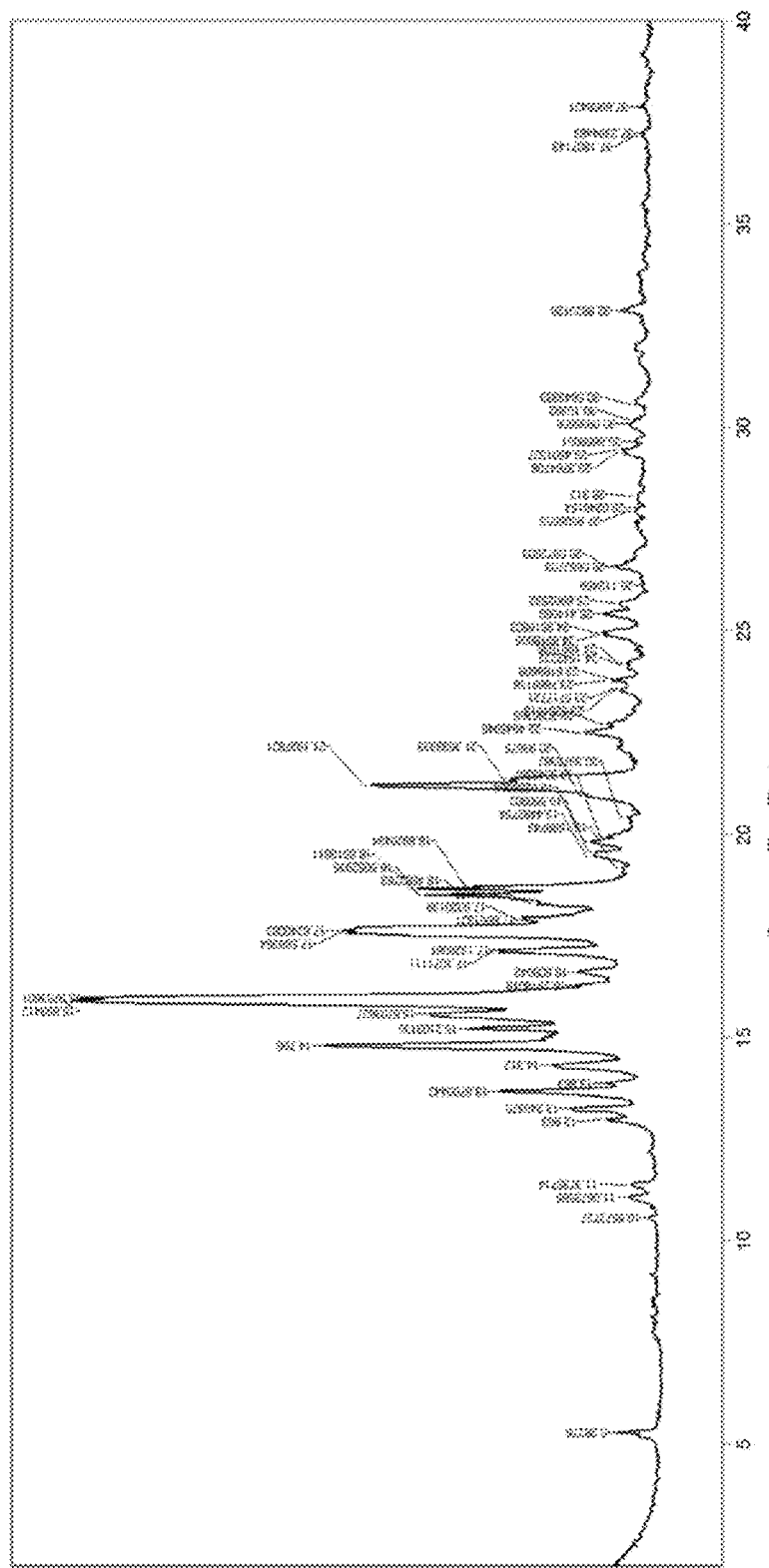
FIG. 31 illustrates a diffractogram of XRPD 3528.
Figure 32:
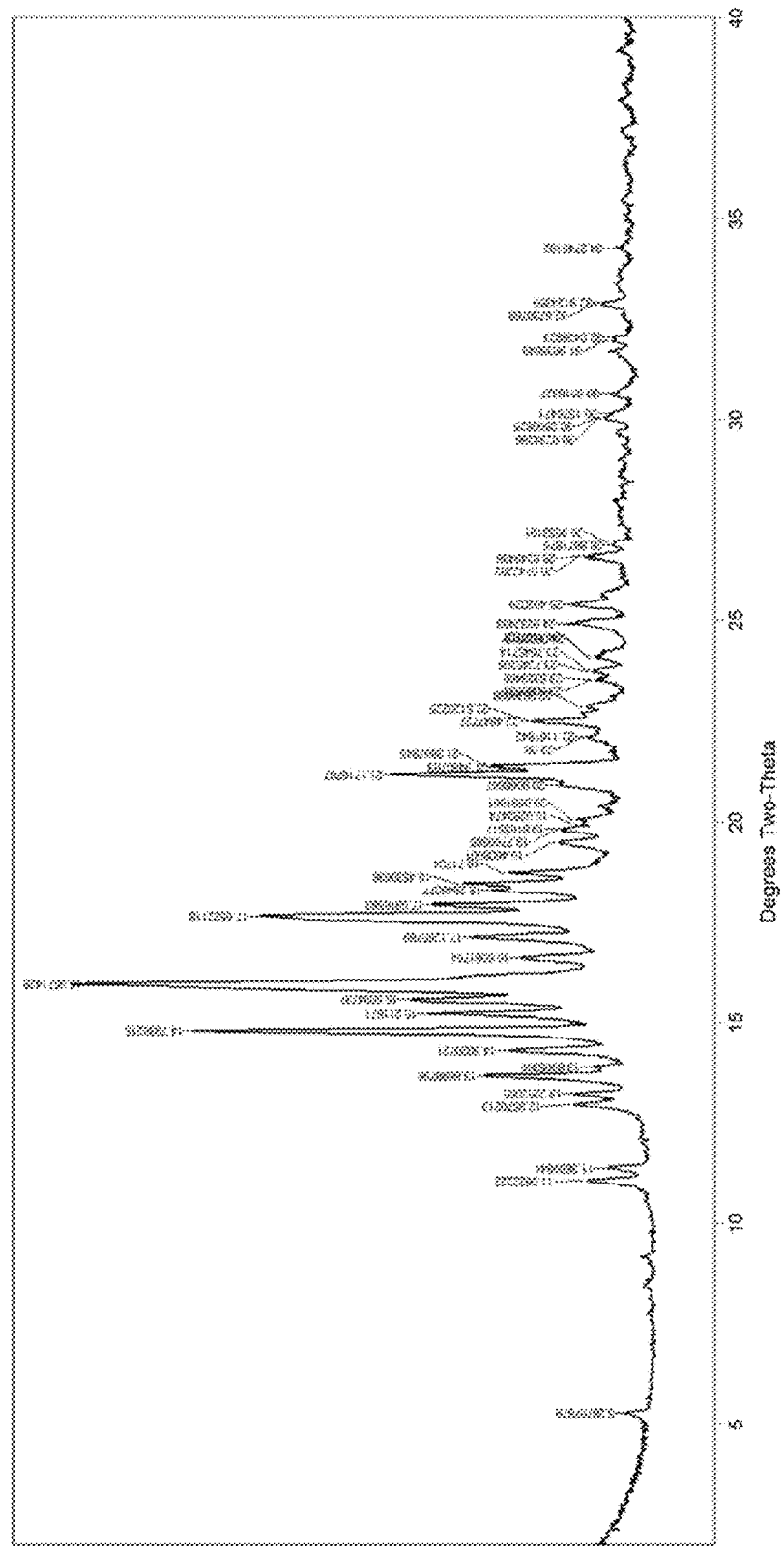
FIG. 32 illustrates a diffractogram of XRPD 3834.
Figure 33:
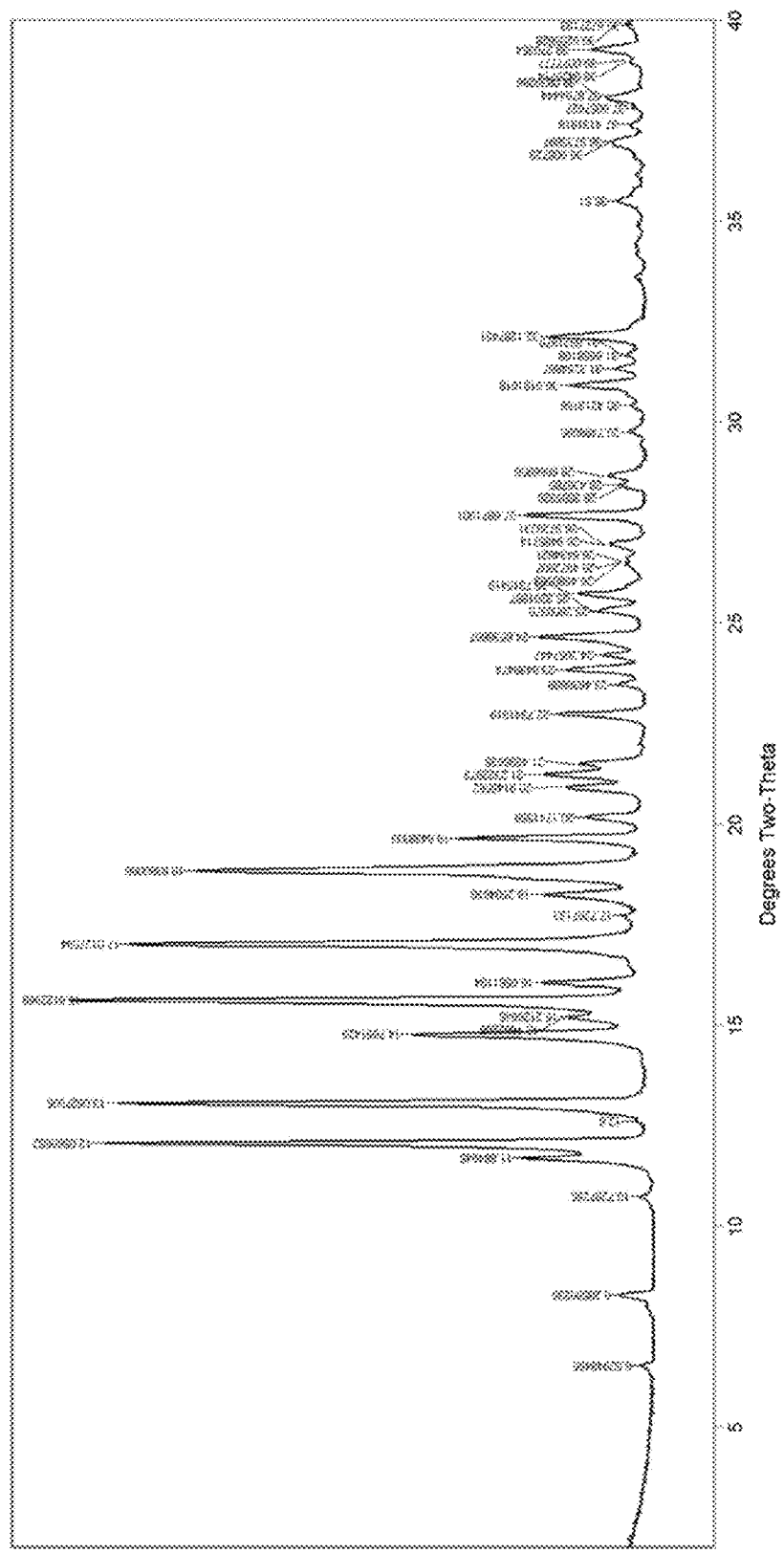
FIG. 33 illustrates a diffractogram of XRPD 3832.
Figure 34:
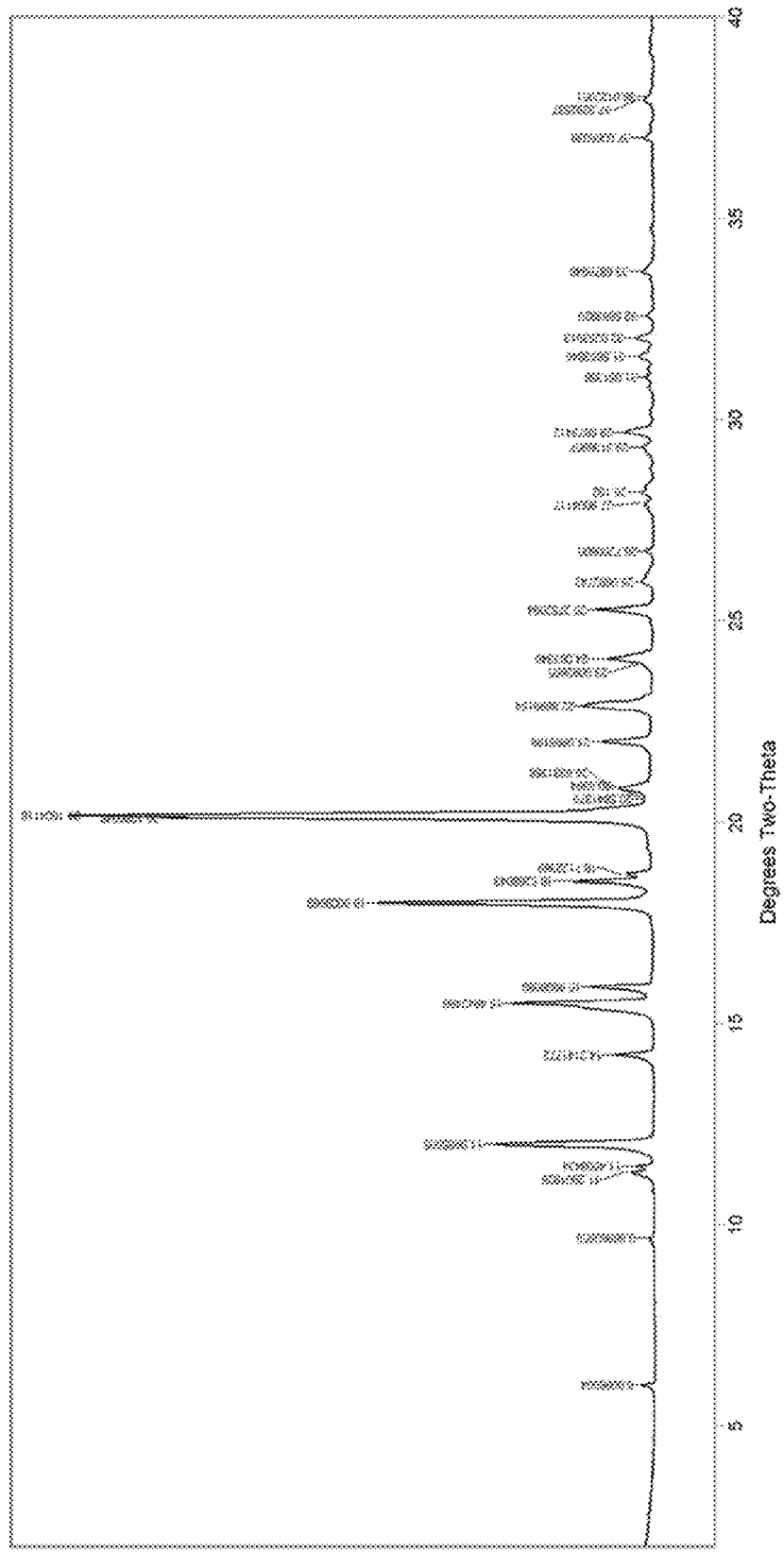
FIG. 34 illustrates a diffractogram of XRPD 3517.
Figure 35:
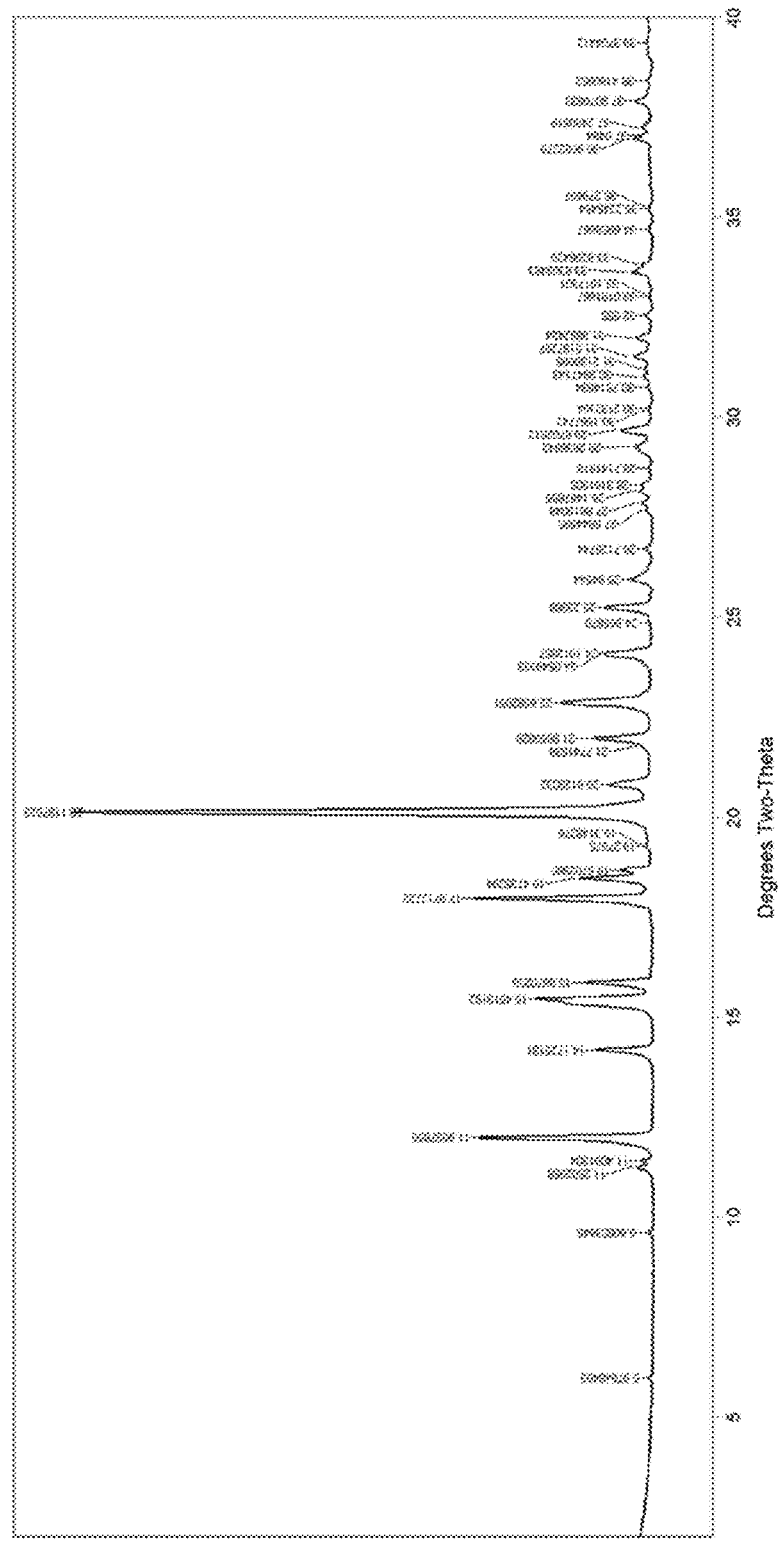
FIG. 35 illustrates a diffractogram of XRPD 3828.
Figure 36:
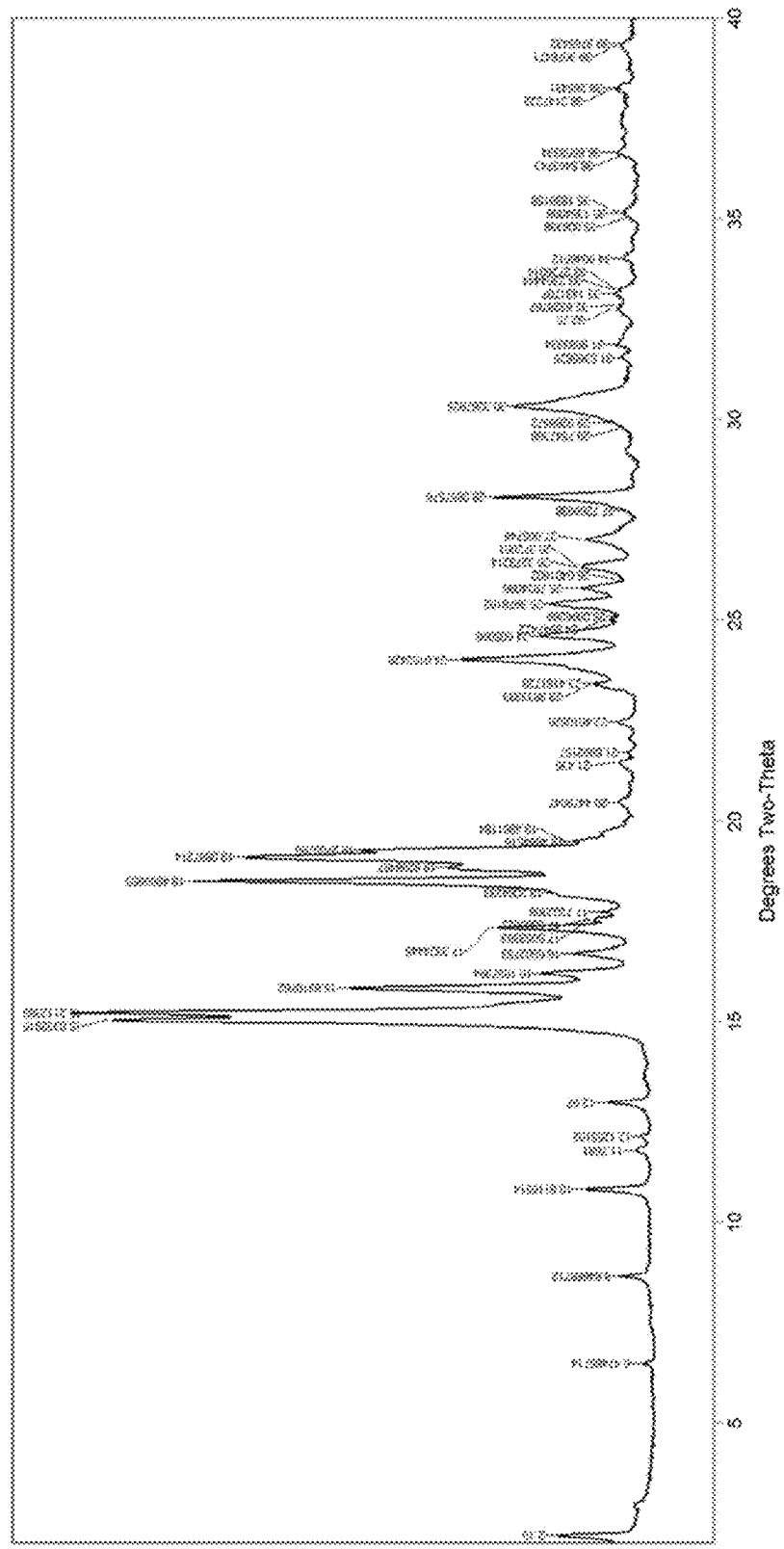
FIG. 36 illustrates a diffractogram of XRPD 3518.
Figure 37:
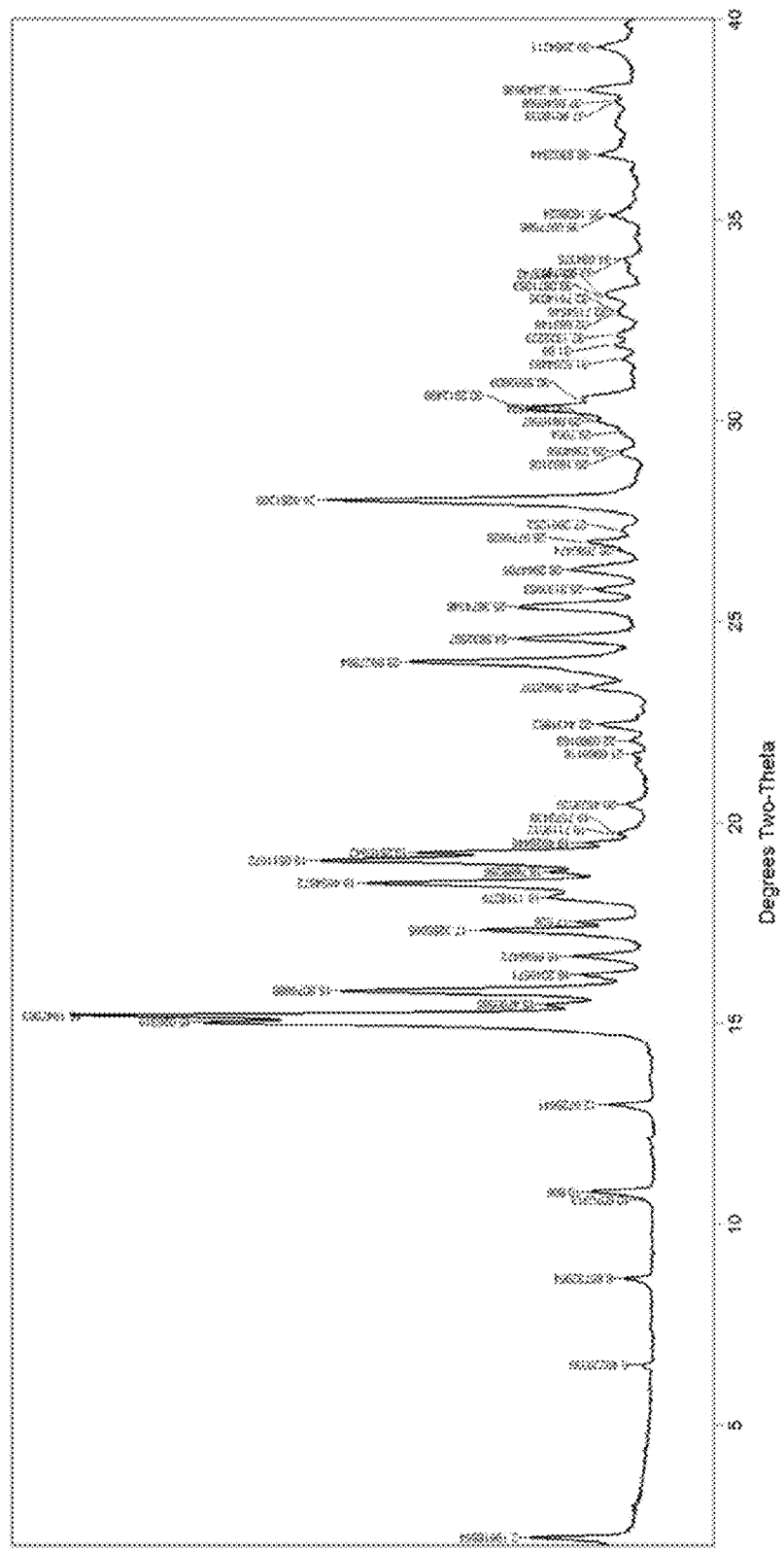
FIG. 37 illustrates a diffractogram of XRPD 3829.
Figure 38:
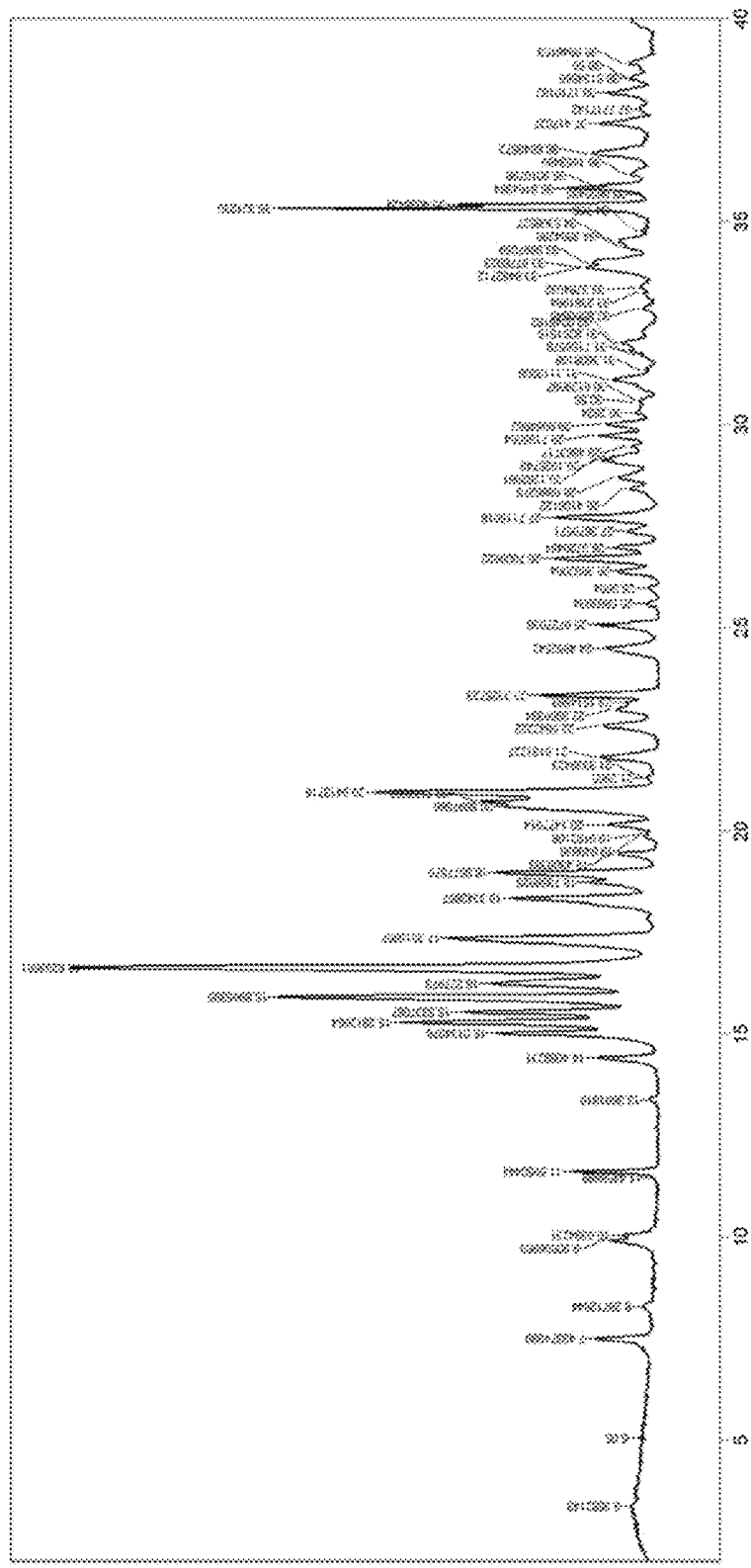
FIG. 38 illustrates a diffractogram of XRPD 3860.
Figure 39:
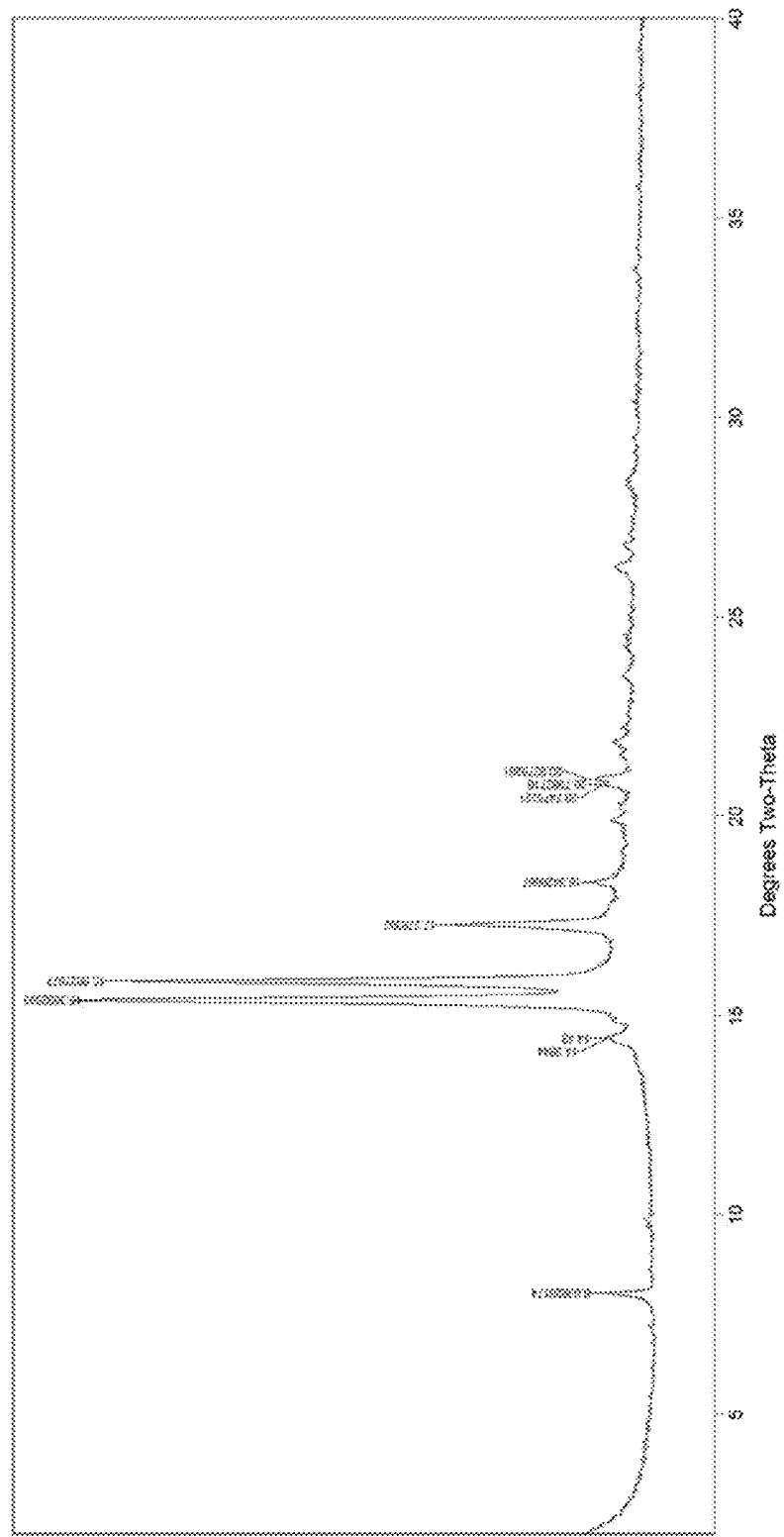
FIG. 39 illustrates a diffractogram of XRPD 3132.
Figure 40:
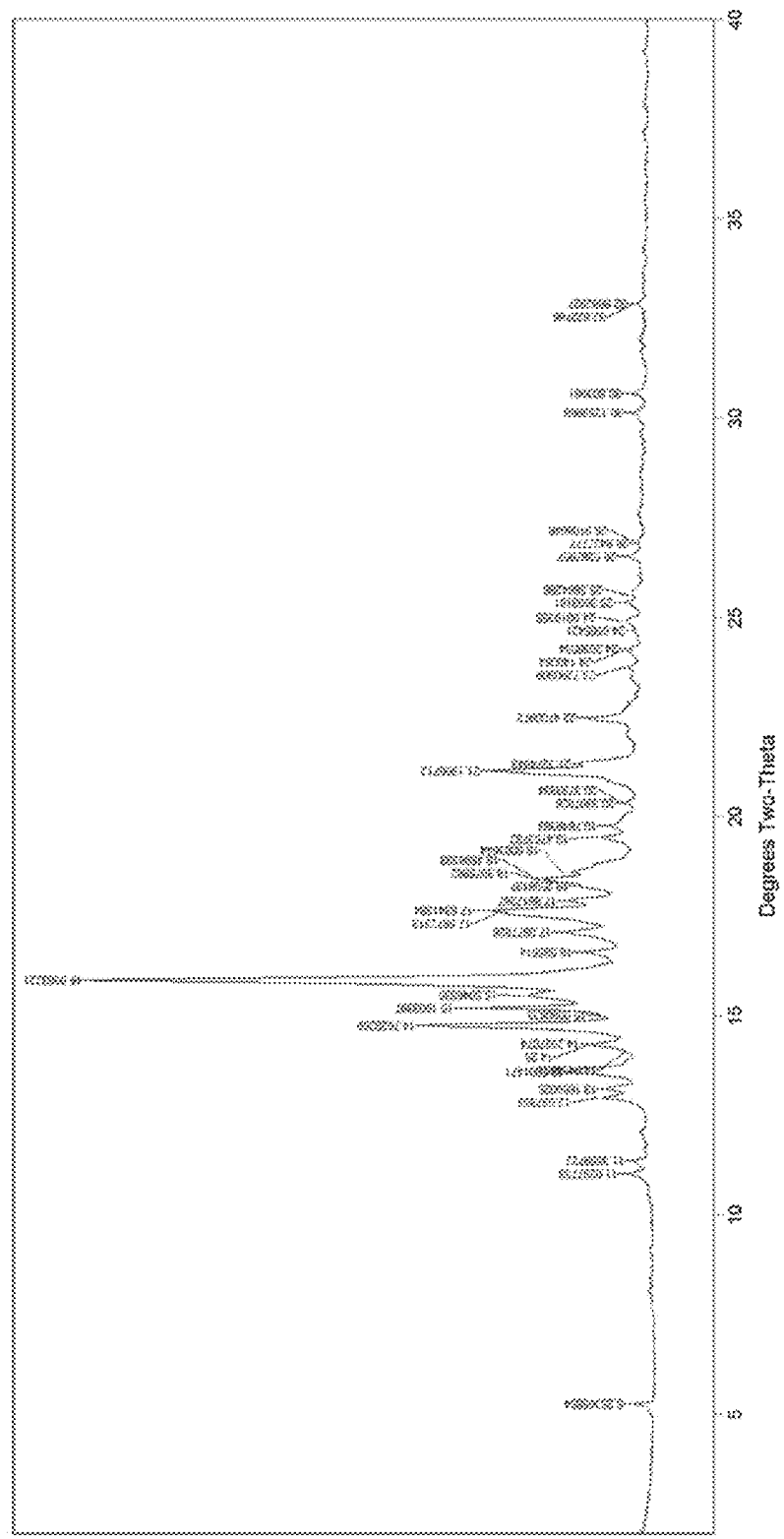
FIG. 40 illustrates a diffractogram of XRPD 3167.
Figure 41:
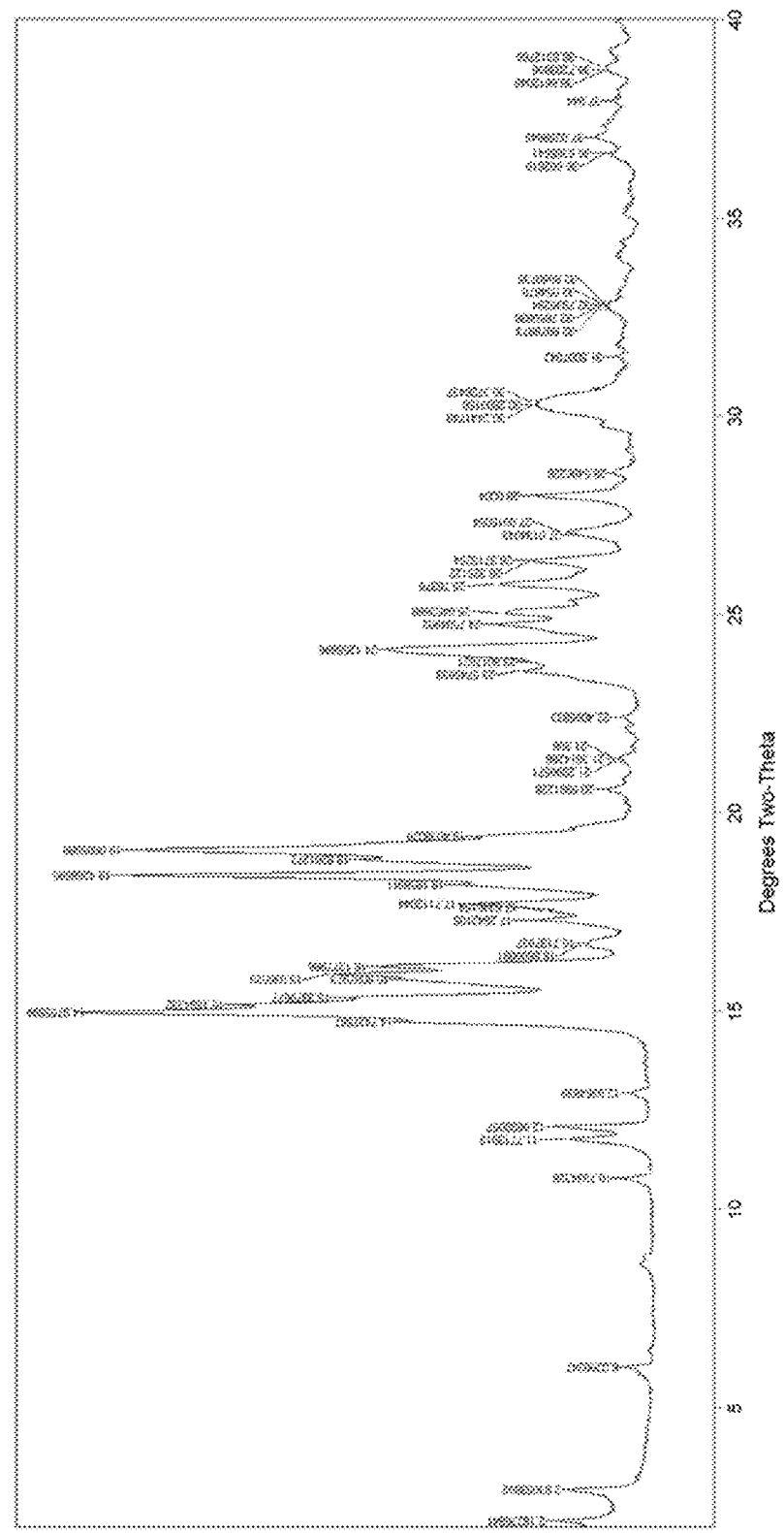
FIG. 41 illustrates a diffractogram of XRPD 3045.
Figure 42:
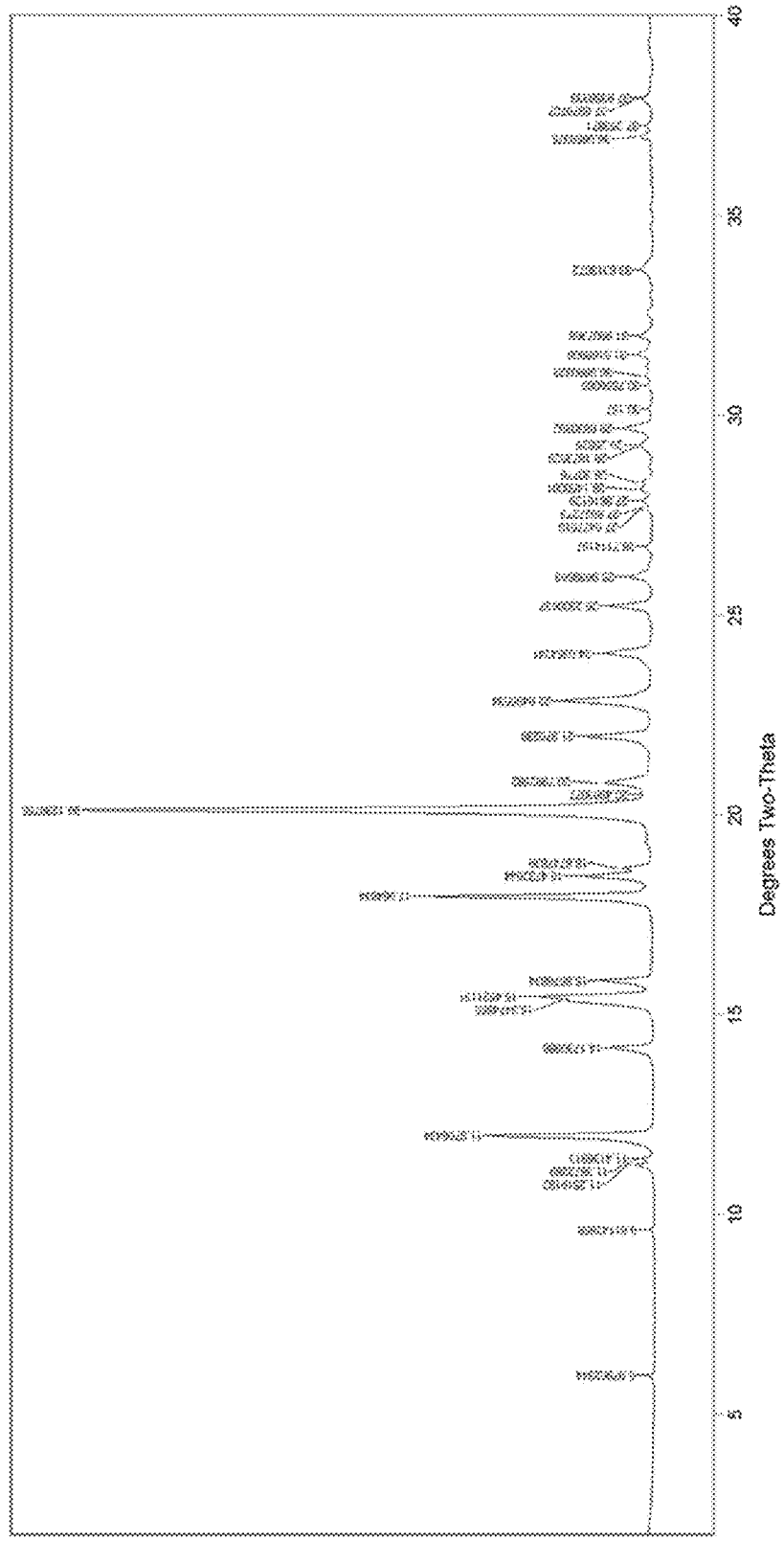
FIG. 42 illustrates a diffractogram of XRPD 3044.
Figure 43:
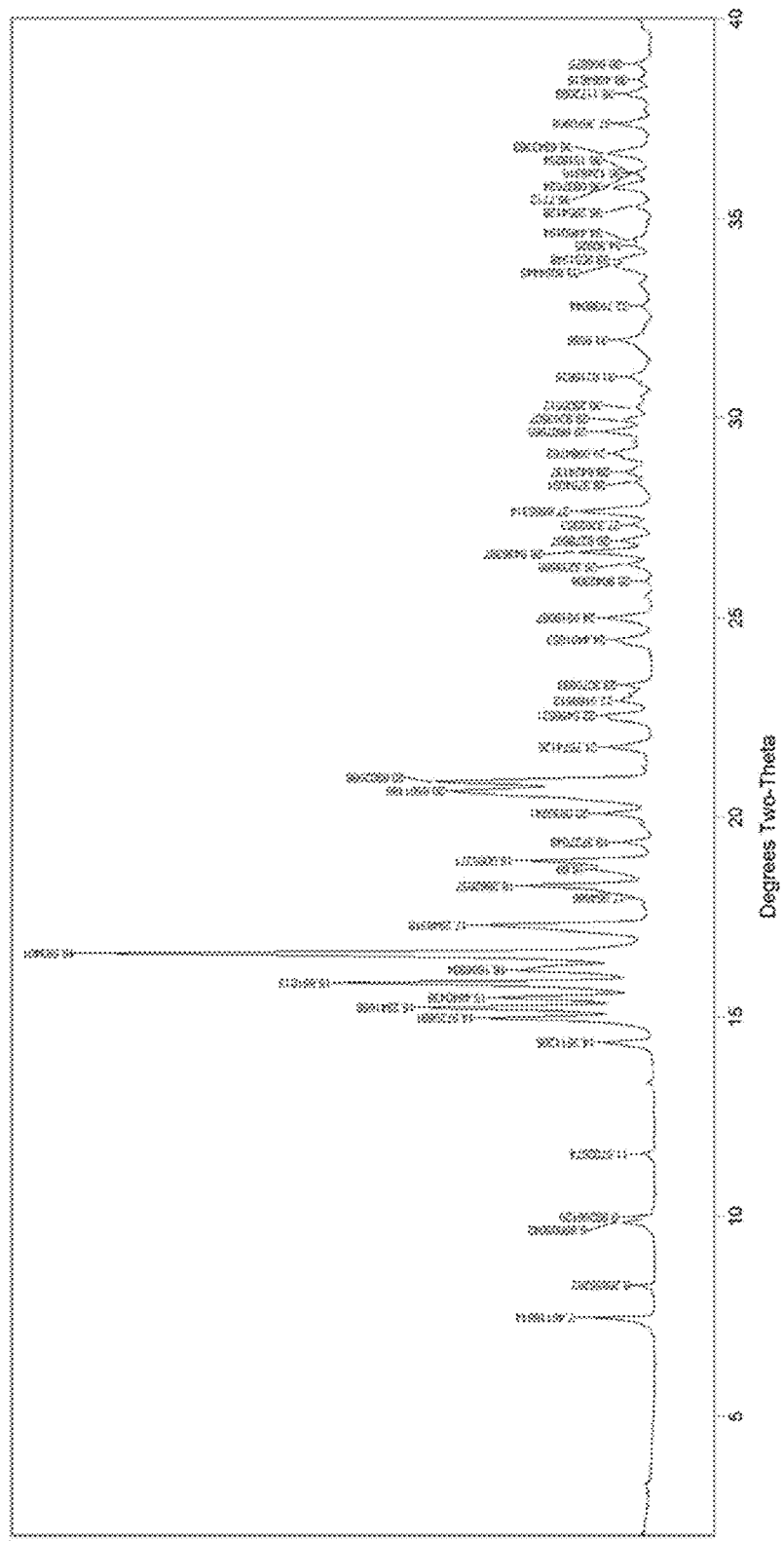
FIG. 43 illustrates a diffractogram of XRPD 3072.

Dissolution data for the formulated DHEA/D-fructose cocrystal are graphed in FIG. 28. A maximum concentration of 236 µg/mL (about 1.7× supersaturated) was achieved and supersaturation was maintained for about one hour. The dissolution data for the formulated DHEA/maleic acid cocrystal are plotted in FIG. 29. A maximum concentration of 148 µg/mL (about 1.2× supersaturated) was achieved and supersaturation was maintained for about one hour. For comparison FIG. 30 illustrates a graph of the dissolution of unformulated DHEA Form FI in simulated intestinal fluid.

Further, two cocrystals were prepared in large enough quantities to be used in dissolution, the DHEA/D-fructose cocrystal was made by cooling a melt containing equimolar amounts of the components. The DHEA/maleic acid cocrystal was made by rapid evaporation of solvent from a solution containing equimolar amounts of the components. The samples prepared exhibited XRPD patterns consistent with previously-prepared samples. FIGS. 31 through 43 illustrate the XRPD pattern peak graphs of the samples described in FIG. 4. Further slurry formulations were used for cocrystal dissolution experiments. Such formulations are often used in pre-clinical, in vivo studies. It is anticipated that medical testing will use slurry formulations of DHEA cocrystals for rat gavage PK studies. Since slurries can be prepared immediately before administration, the cocrystals need not be stable in the slurry fluid.

Figure 44:
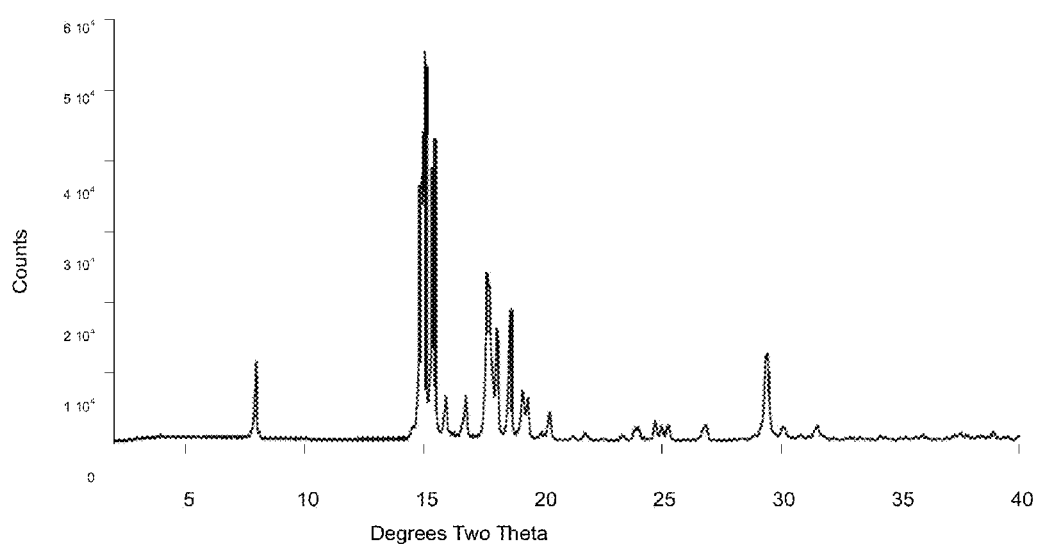
FIG. 44 illustrates a diffractogram containing the data from XRPD 3167 showing that the starting DHEA is of anhydrous F1 form.
Figure 45:
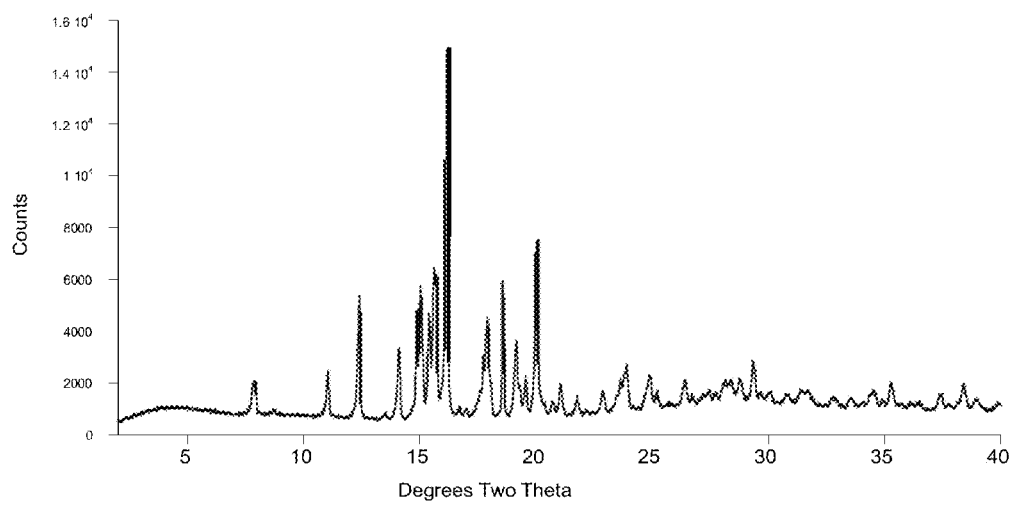
FIG. 45 illustrates a difractogram containing the data from XRPD 3171 showing that a sample of DHEA anhydrate F1 slurried in SIF for about 3 hrs at room temperature was mostly the hydrate S1 form.
Figure 47:
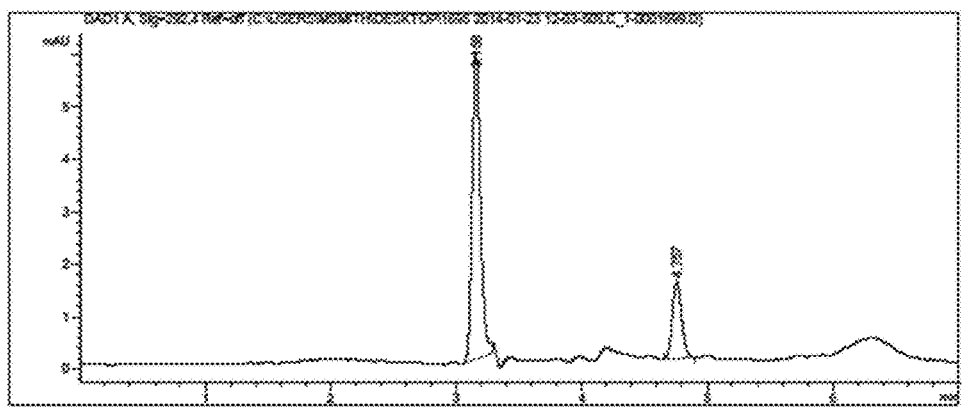
FIG. 47 illustrates a graph containing the data from HPLC 1669.
Figure 48:
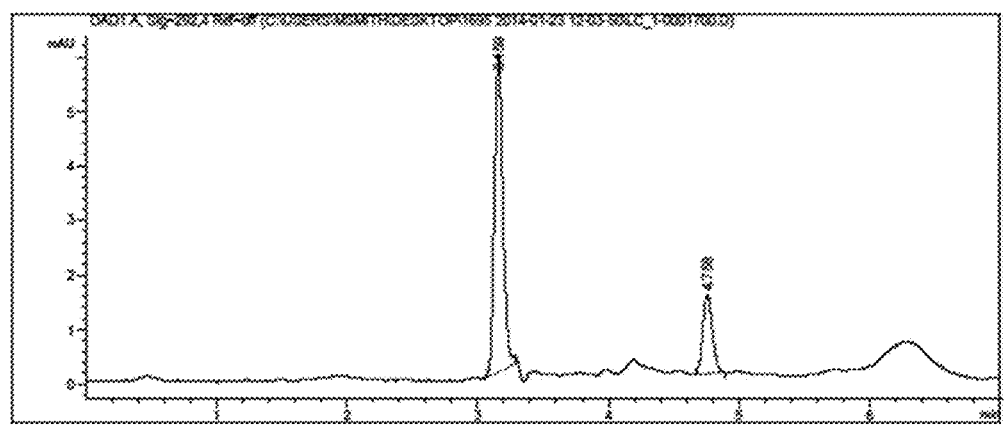
FIG. 48 illustrates a graph containing the data from HPLC 1700.
Figure 49:
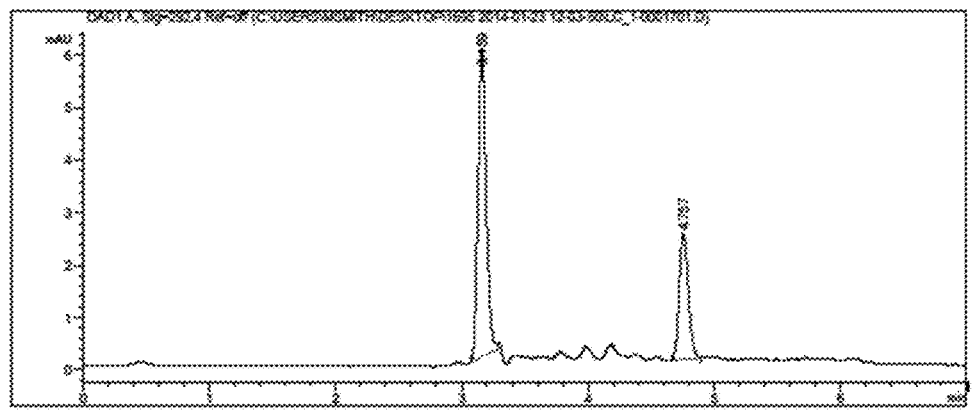
FIG. 49 illustrates a graph containing the data from HPLC 1701.
Figure 50:
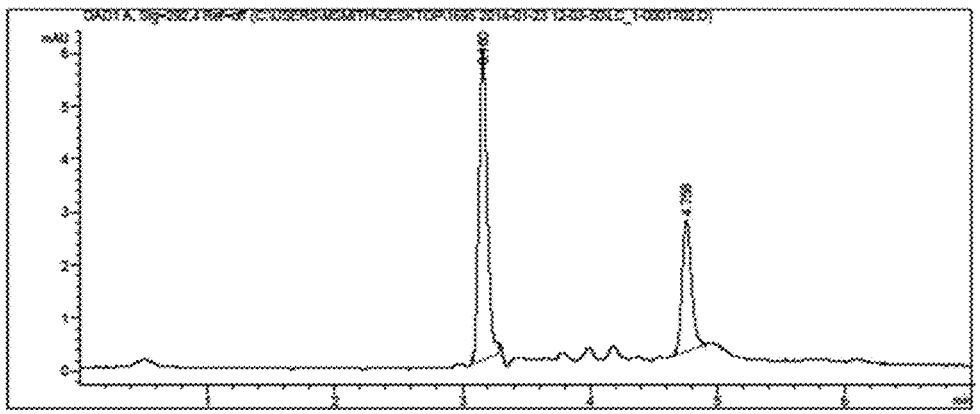
FIG. 50 illustrates a graph containing the data from HPLC 1702.
Figure 51:
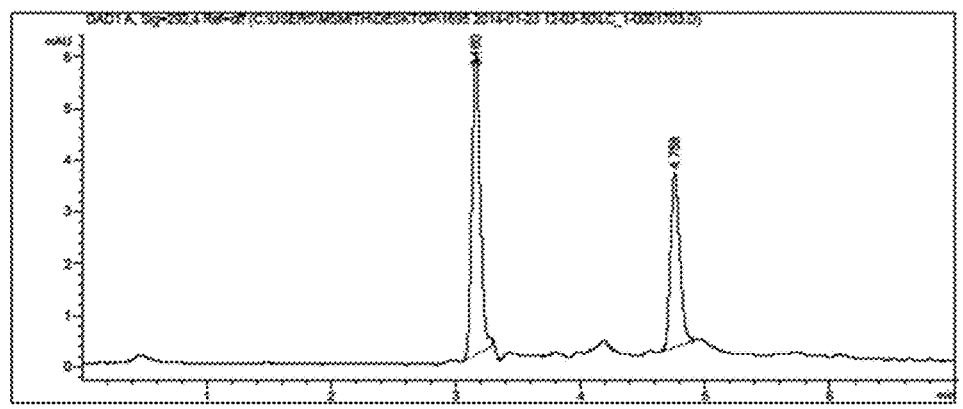
FIG. 51 illustrates a graph containing the data from HPLC 1703.
Figure 52:
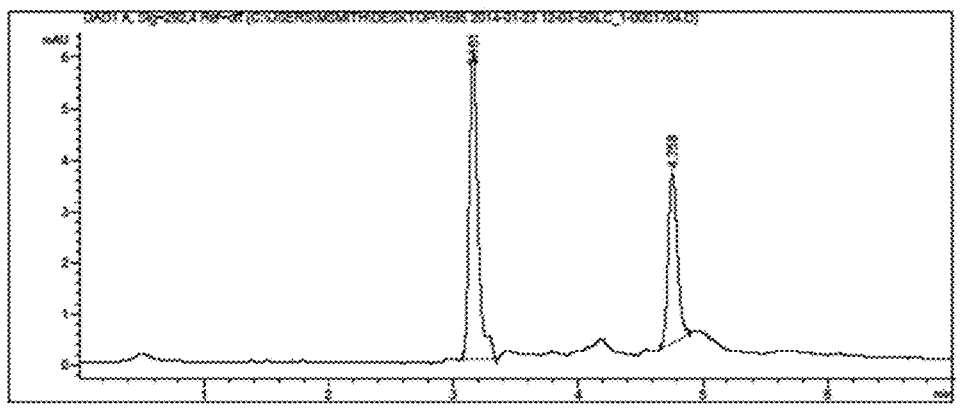
FIG. 52 illustrates a graph containing the data from HPLC 1704.
Figure 53:
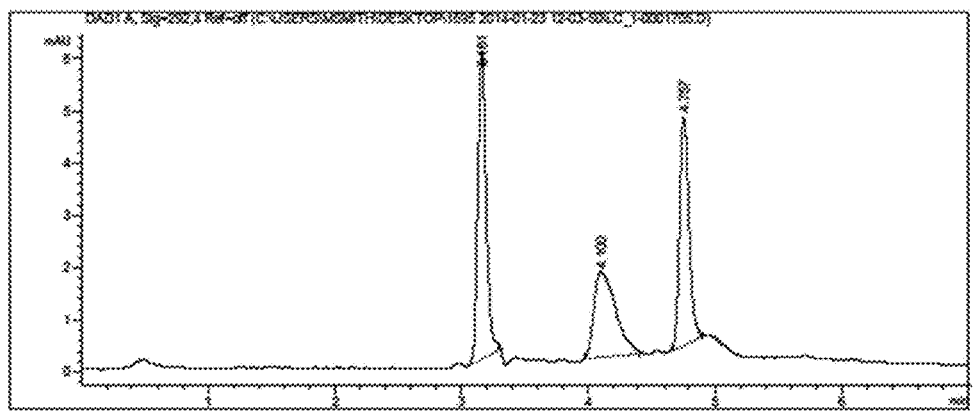
FIG. 53 illustrates a graph containing the data from HPLC 1705.
Figure 54:
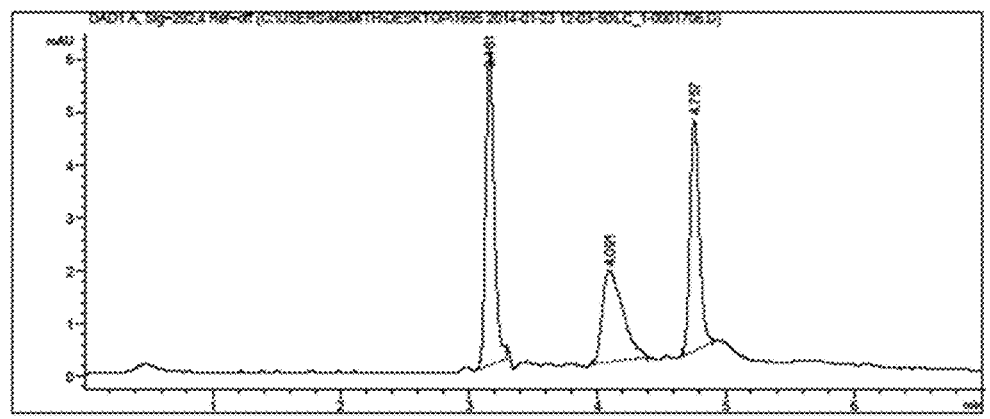
FIG. 54 illustrates a graph containing the data from HPLC 1706.
Figure 55:
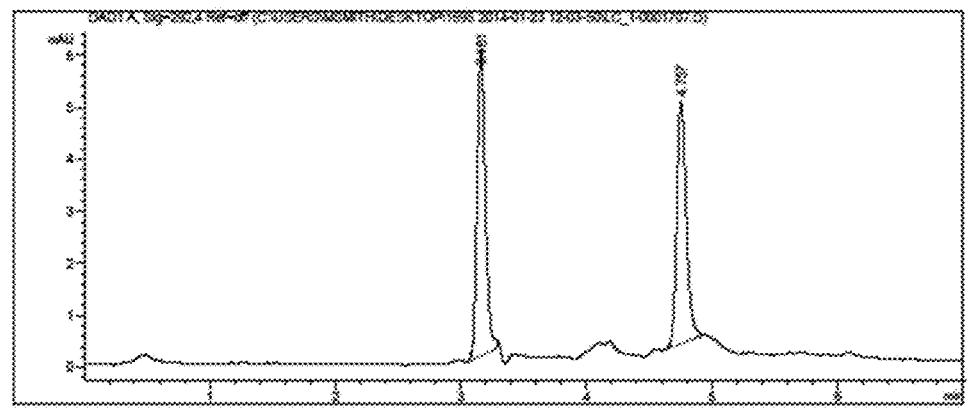
FIG. 55 illustrates a graph containing the data from HPLC 1707.
Figure 56:
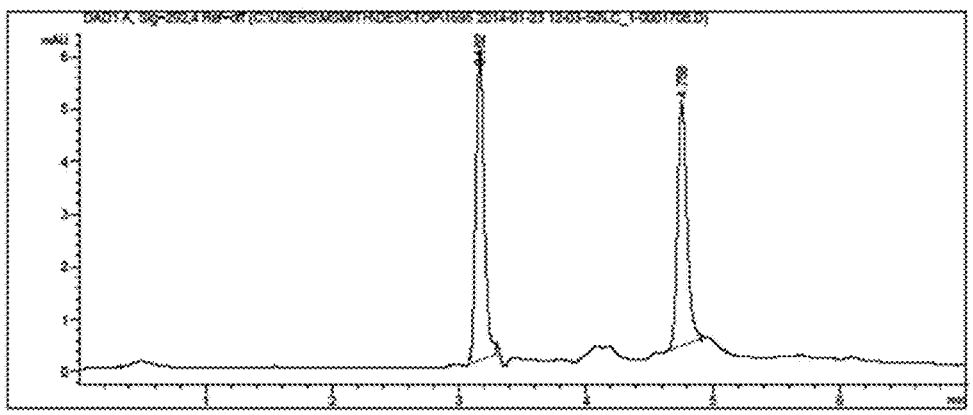
FIG. 56 illustrates a graph containing the data from HPLC 1708.
Figure 57:
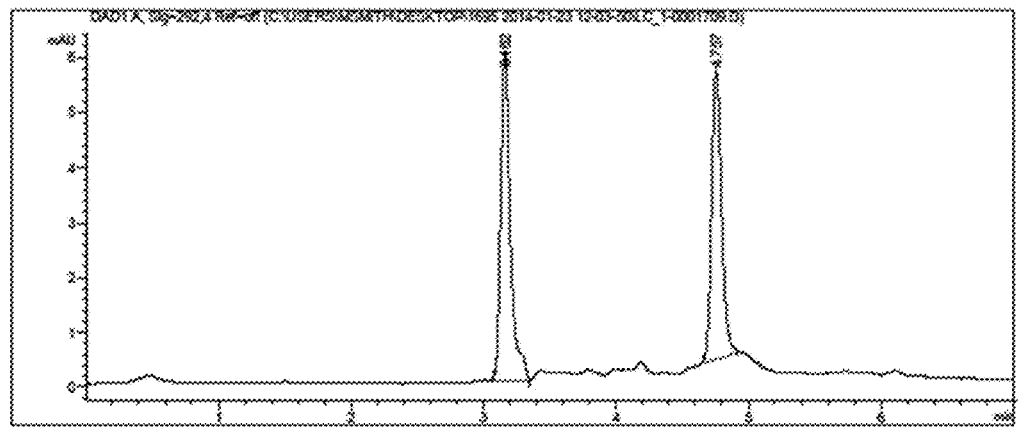
FIG. 57 illustrates a graph containing the data from HPLC 1709.
Figure 58:
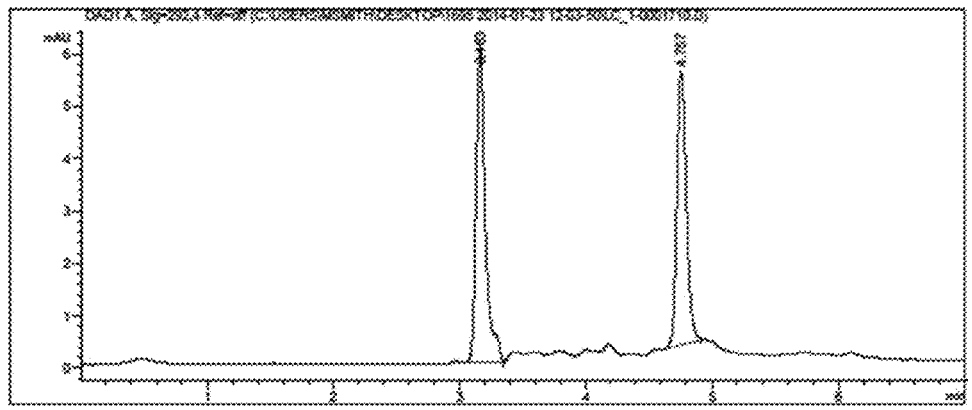
FIG. 58 illustrates a graph containing the data from HPLC 1710.
Figure 59:
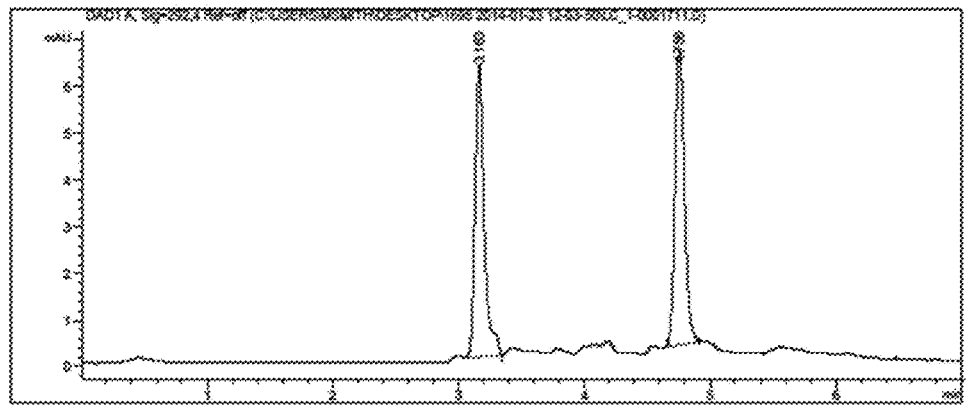
FIG. 59 illustrates a graph containing the data from HPLC 1711.
Figure 60:
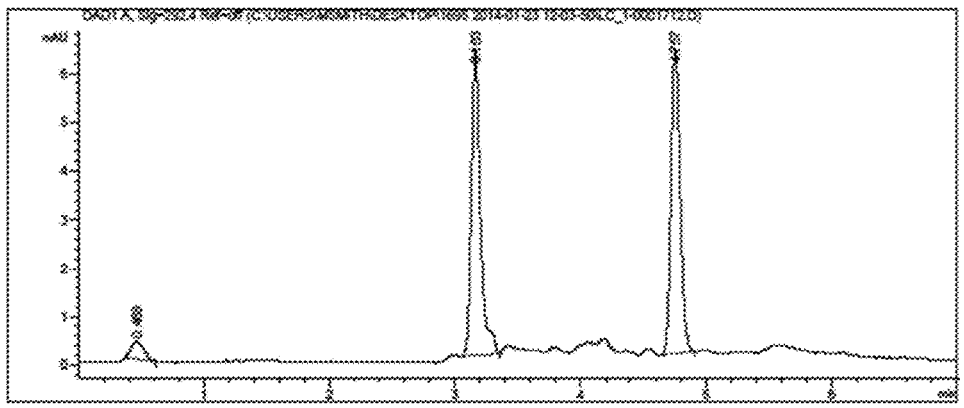
FIG. 60 illustrates a graph containing the data from HPLC 1712.
Figure 61:
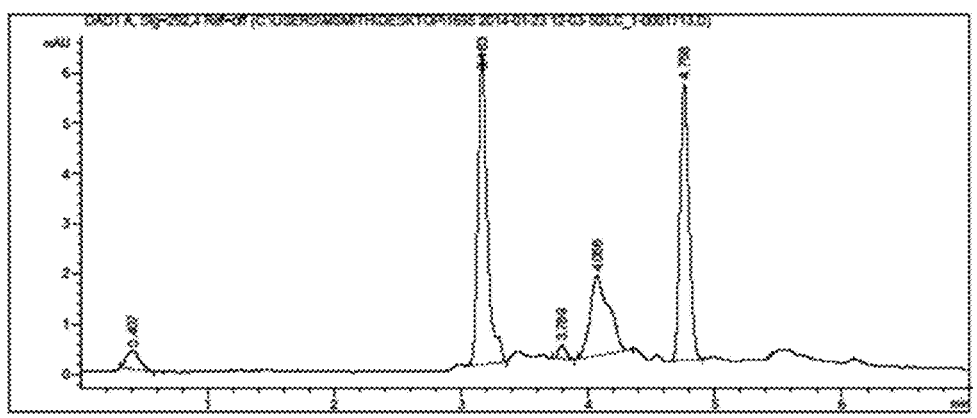
FIG. 61 illustrates a graph containing the data from HPLC 1713.
Figure 62:
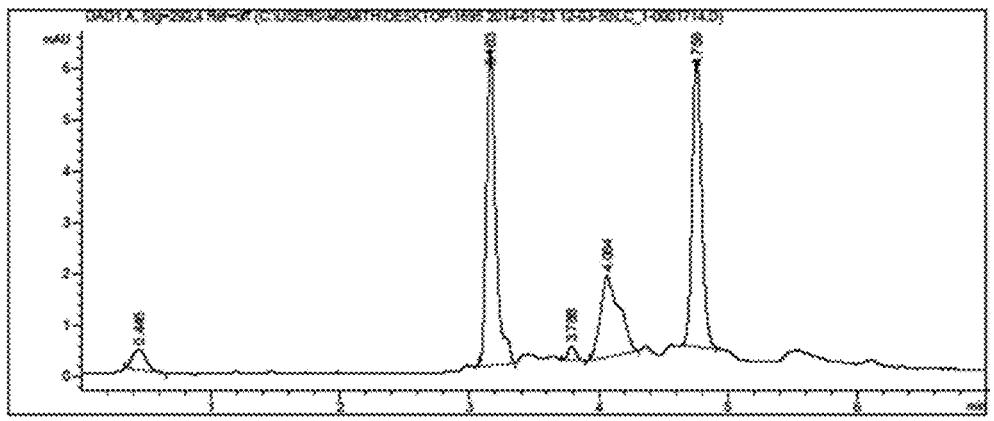
FIG. 62 illustrates a graph containing the data from HPLC 1714.
Figure 63:
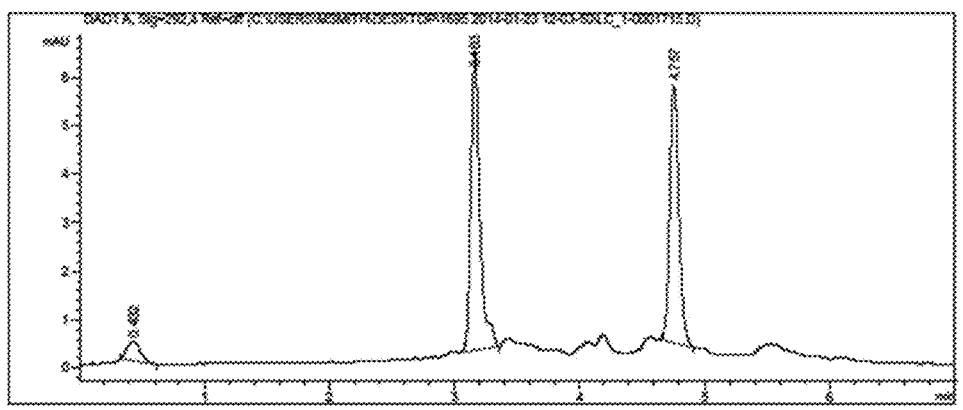
FIG. 63 illustrates a graph containing the data from HPLC 1715.

For FIGS. 44 and 45, to the 30 mL-vial of SIF (20-mL vial was charged with 10 mL of water and placed in a 37° C. bath) 12.1 mg of DHEA (from sample TL876) was added. The vial was capped and shaken, and the resulting slurry was poured into the round-bottom flask. A timer was started. At appropriate intervals approximately 1.3 mL of slurry was removed from the flask and passed through a 0.5-µm PTFE filter. One mL of each filtrate was placed in an open vial and purged with dry air until the water evaporated. The vials were placed in a vacuum desiccator for a short time. Each vial was charged with 0.5 mL of acetonitrile and a stir bar. The slurries were stirred at ambient temperature for about one hour and centrifuged for about ten minutes. The supernatants were analyzed by HPLC. FIGS. 47 through 68 illustrate the HPLC peaks from the supernatants recovered from the dissolution experiments prepared as described hereinabove.

Various embodiments are disclosed herein. Variations, combinations, and/or modifications of the embodiments and/or features of the embodiments made by a person having ordinary skill in the art are within the scope of the disclosure. Alternative embodiments that result from combining, integrating, and/or omitting features of a disclosed embodiment or embodiments are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as "comprises", "includes", and "having" should be understood to provide support for narrower terms such as "consisting of", "consisting essentially of", and "comprised substantially of". Accordingly, the scope of protection is not limited by the description set out above but is defined by the claims that follow, that scope including all equivalents of the subject matter of the claims. Each and every claim is incorporated as further disclosure into the specification and each of the claims is an exemplary embodiment of the present invention. The discussion of a reference in the disclosure is not an admission that it is prior art, especially any reference that has a publication date after the priority date of this application. The disclosure of all patents, patent applications, and publications cited in the disclosure are hereby incorporated by reference, to the extent that they provide exemplary, procedural or other details supplementary to the disclosure.

What is claimed is:

1. A composition formulated to produce a supersaturated intestinal solution, said composition comprising:
    dehydroepiandrosterone (DHEA), wherein the DHEA is a polymorph form I (FI) or polymorph form II (FII); and
    a crystalline coformer selected from the group consisting of fructose and maleic acid, wherein the DHEA and the coformer are in an approximately 1:1 molar stoichiometric ratio; and wherein said supersaturated intestinal solution is maintained at between 50 micrograms/ml and 236 micrograms/ml for between 60 minutes and 240 minutes.

2. The composition of claim 1, wherein the DHEA and the coformer form a cocrystalline formulation.

3. The composition of claim 2, wherein the cocrystalline formulation dissolves in an aqueous solution.

4. The composition of claim 3, wherein the cocrystalline formulation dissolves to form a supersaturated aqueous solution.

5. The composition of claim 1, wherein the composition further comprises at least one excipient.

6. The composition of claim 5, wherein the excipient is selected from the group consisting of polyethylene glycol (PEG), poly-vinylpyrrolidone (PVP), vinylpyrrolidone vinylacetate copolymer (PLASDONE™ S-630) and polyoxyethylene-sorbitan-mono-oleate ester (POLYSORBATE 80).

7. A cocrystalline composition comprising
    dehydroepiandrosterone (DHEA); wherein the DHEA is a polymorph form I (FI) or polymorph form II (FII); and a coformer selected from the group consisting of fructose and maleic acid, wherein the DHEA and the coformer are in an approximately 1:1 molar stoichiometric ratio; and an excipient, wherein said cocrystalline composition is about three times more soluble in an intestinal fluid than DHEA itself.

8. The composition of claim 7, wherein the excipient is selected from the group consisting of polyethylene glycol (PEG), poly-vinylpyrrolidone (PVP), vinylpyrrolidoneviny-lacetate copolymer (PLASDONE™ S-630), and polyoxyethylene-sorbitan-mono-oleate ester (POLYSORBATE 80).

9. The composition of claim 7, wherein the excipient has a concentration of less than about 10% by weight.

10. A method for treating a neurological disease in a patient comprising:
 identifying a neurological disease symptom in the patient;
 determining the patient's tolerance to at least one crystalline coformer, wherein the coformer is selected from the group consisting of fructose and maleic acid;
 providing the patient a cocrystalline formulation comprising DHEA, and the at least one coformer,
 wherein said cocrystalline formulation forms a supersaturated intestinal solution;
 wherein the supersaturated solution contains DHEA at between 50 and 236 micrograms/ml for between 60 and 240 minutes;
 analyzing a response by the patient to the formulation; and
 adjusting the cocrystalline formulation according to the patient's response.

11. The method of claim 10, wherein the cocrystalline formulation further comprises an excipient.

12. The method of claim 11, wherein the excipient is at least one chosen from the group consisting of polyethylene glycol (PEG), poly-vinylpyrrolidone (PVP), vinylpyrrolidone-vinylacetate copolymer (PLASDONE™ S-630), and polyoxyethylene-sorbitan-mono-oleate ester (POLYSORBATE 80).

13. A composition comprising:
 a cocrystal, wherein the cocrystal comprises:
  dehydroepiandrosterone (DHEA), wherein the DHEA is a polymorph form I (FI) or polymorph form II (FII); and
  a coformer, wherein the coformer is selected from the group consisting of fructose and maleic acid, wherein the DHEA and the coformer are in an approximately 1:1 molar stoichiometric ratio; and wherein said cocrystal is about three times more intestinal soluble than DHEA itself.

14. A composition formulated to delay recrystallization of dehydroepiandrosterone (DHEA) from an aqueous intestinal solution, wherein said composition comprises:
 dehydroepiandrosterone (DHEA) polymorph form I (FI); and a maleic acid cocrystal, wherein the DHEA and the maleic acid cocrystal are in approximately a 1:1 molar stoichiometric ratio, and wherein said aqueous intestinal solution is at a concentration of between 50 and 148 micrograms/ml for about 60 minutes prior to recrystallization.

15. A composition formulated to delay recrystallization of dehydroepiandrosterone (DHEA) polymorph form I (FI) from an aqueous intestinal solution wherein said composition comprises:
 dehydroepiandrosterone (DHEA) polymorph form I (FI); and a crystalline coformer, wherein the coformer is fructose, and said conformer and the DHEA are in approximately a 1:1 molar stoichiometric ratio, and wherein said aqueous intestinal solution is at a concentration of between 50 and 236 micrograms/ml for about 60 minutes prior to recrystallization.

* * * * *